United States Patent
Mcbride et al.

(10) Patent No.: US 11,734,650 B2
(45) Date of Patent: *Aug. 22, 2023

(54) SYSTEM AND METHOD FOR TRANSFERRING DATA

(71) Applicant: Mend VIP, Inc., Orlando, FL (US)

(72) Inventors: Matthew D. Mcbride, Orlando, FL (US); Brandon Lassiter, Orlando, FL (US); Paul Senzee, Apopka, FL (US); Alexander Decurnou, Winter Park, FL (US); Jessica Hoffman, Orlando, FL (US); Gabriel Latorre, Orange City, FL (US)

(73) Assignee: Mend VIP, Inc., Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/970,147

(22) Filed: Oct. 20, 2022

(65) Prior Publication Data

US 2023/0090564 A1 Mar. 23, 2023

Related U.S. Application Data

(63) Continuation of application No. 17/201,372, filed on Mar. 15, 2021, now abandoned, which is a
(Continued)

(51) Int. Cl.
*G06F 21/31* (2013.01)
*G06Q 10/1093* (2023.01)
(Continued)

(52) U.S. Cl.
CPC ......... *G06Q 10/1093* (2013.01); *G06F 21/31* (2013.01); *G06N 20/20* (2019.01);
(Continued)

(58) Field of Classification Search
CPC .. G06F 21/31; G06F 2221/2137; G16H 40/20
See application file for complete search history.

(56) References Cited

U.S. PATENT DOCUMENTS

| 7,725,342 B2 | 5/2010 | Koehane et al. |
| 2005/0027567 A1 | 2/2005 | Taha |

(Continued)

OTHER PUBLICATIONS

Optimizing outpatient appointment system using machine learning algorithms and scheduling rules: A prescriptive analytics framework: S Srinivas, AR Ravindran—Expert Systems with Applications, 2018—Elsevier (Year: 2018).

(Continued)

*Primary Examiner* — Nelson S. Giddins
(74) *Attorney, Agent, or Firm* — Maier & Maier, PLLC

(57) ABSTRACT

An efficient and secure process by which users may enter sensitive information into an electronic information system. When information is required from a user, the electronic information system may be configured to generate a unique access link (uniform resource locator, or URL) for that user. The link may be sent to the user via electronic communication, such as a text message or email. When the user follows the link with a web browser, the system prompts the user to enter an additional piece of personal information that is not known to the general public. Once identity is verified, the user may be required to electronically sign agreements. The user is then prompted to enter the required information. This may allow a user to deposit sensitive information into the system without requiring the user to provide full login credentials.

20 Claims, 36 Drawing Sheets

Related U.S. Application Data continuation-in-part of application No. 16/993,564, filed on Aug. 14, 2020, now Pat. No. 11,055,434, which is a continuation of application No. 15/923,333, filed on Mar. 16, 2018, now Pat. No. 10,776,512.

(60) Provisional application No. 62/472,927, filed on Mar. 17, 2017.

(51) Int. Cl.
  *G16H 40/20* (2018.01)
  *G06Q 10/0631* (2023.01)
  *G06N 20/20* (2019.01)

(52) U.S. Cl.
  CPC ....... *G06Q 10/06314* (2013.01); *G16H 40/20* (2018.01); *G06F 2221/2137* (2013.01)

(56) References Cited

U.S. PATENT DOCUMENTS

| | | | | |
|---|---|---|---|---|
| 2006/0227378 | A1* | 10/2006 | Mihira | G06F 21/6218 358/402 |
| 2013/0317873 | A1 | 11/2013 | Kozloski et al. | |
| 2014/0316797 | A1 | 10/2014 | Biernacki et al. | |
| 2015/0271241 | A1 | 9/2015 | Sun et al. | |
| 2016/0357981 | A1* | 12/2016 | Tzeng | G06F 21/6218 |
| 2017/0083534 | A1* | 3/2017 | Strong | H04L 63/168 |
| 2017/0169168 | A1 | 6/2017 | Batchelor et al. | |
| 2017/0272426 | A1 | 9/2017 | Wertz | |
| 2017/0351866 | A1 | 12/2017 | Goh et al. | |
| 2019/0205905 | A1 | 7/2019 | Raghunathan et al. | |
| 2019/0205939 | A1 | 7/2019 | Lal et al. | |
| 2020/0117748 | A1 | 4/2020 | Gupte et al. | |
| 2020/0302358 | A1 | 9/2020 | McBride et al. | |

OTHER PUBLICATIONS

"The Wald problem and the equivalence of sequential sampling and Ex-Ante Information Costs" S Morris, P Strack—Feb. 2019—SSRN (Year: 2019).

Curtailed online boosting R Pelossof, M Jones—2009—academiccommons.columbia.edu (Year: 2009).

A metaheuristic-based stacking model for predicting the risk of patient no show and late cancellation for neurology appointments E Ahmadi, A Garcia-Arce, DT Masel . . . —IISE Transactions on . . . , 2019—Taylor & Francis (Year: 2019).

Patient no-show prediction: A systematic literature review D Carreras-Garcia, D Delgado-Gómez . . . —Entropy, 2020—mdpi.com (Year: 2020).

* cited by examiner

504

506

604

Instant Virtual Exam Room

Provider     Provider, Amy ✕

Patient, Email, or Phone Number *

🔍 Search

Start Date *

Start Time *    03    45    PM

Duration *    15 Minutes

Cancel

Fig. 6C   Your video visit is about to start. Go to https://s.mendvip.com/B4oPu to start

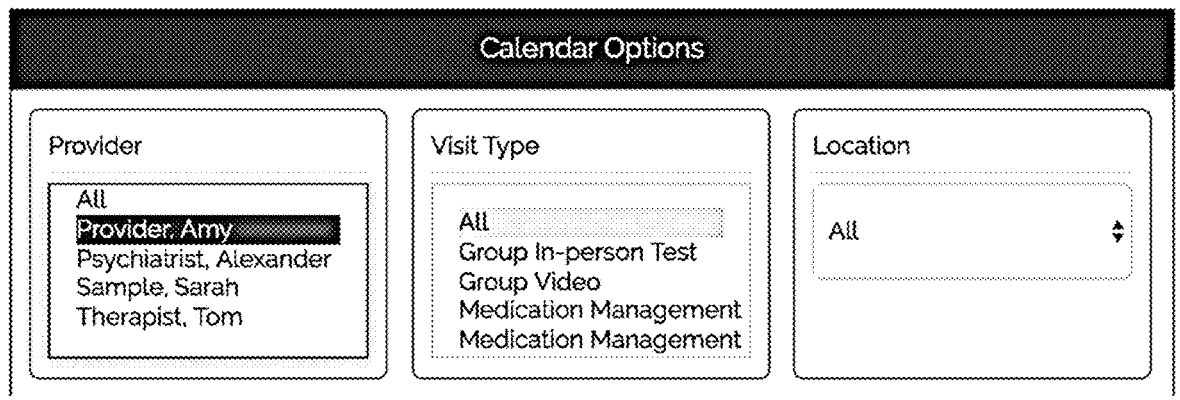
704　　　　　　　　　　Fig. 7B
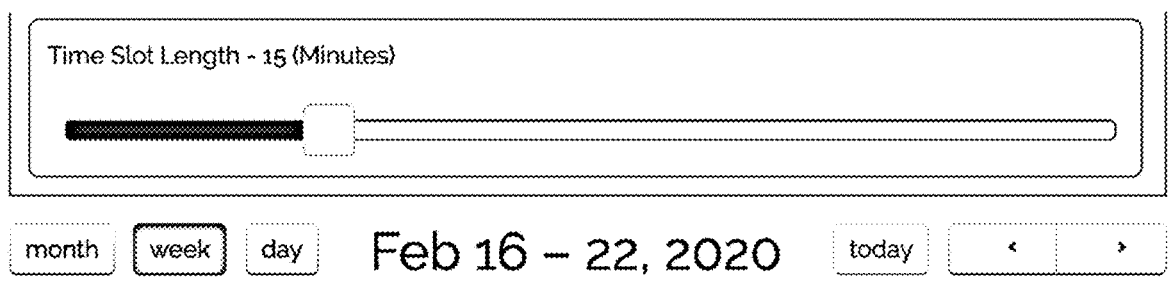
706　　　　　　　　　Fig. 7C

Edit Group Users

Name*

Relapse Prevention Group

Description

Weekly group appointment for relapse prevention.

Selected Users*

No selected users

Users

🔍 search

| First Name | Last Name | Email | BirthDate | Action |
|---|---|---|---|---|
| Sanjay | Gupta | matt+sanjay@mendfamily.co... | 11/23/1969 | ✓ |
| John | Kennedy | matt+kennedy@mendfamily.c... | 05/29/1917 | ✓ |
| Abraham | Lincoln | matt+Lincoln@mendfamily.c... | 02/12/1809 | ✓ |

Edit Group Schedule

| Group Scheduling Enabled | | | | |
|---|---|---|---|---|
| Appointment Type | | | Group Video - 15 minutes | |
| Provider | | | Gupta, Sanjay | |
| Recurring Frequency | | | Every week | |
| Day(s) Of The Week | | S M T W T F S | | |
| Start Date | March | 12 | 2020 | |
| Start Time | 07 | 00 | PM | |
| End Time | 07 | 15 | PM | |

Self Schedule or Patient Schedule?

Do you want to schedule the follow up appointment or allow the patient to schedule?

1020

Follow Up

Provider ▾   Appointment Type ▾

Please select an available time in the white area by clicking a time slot, then click 'Continue'.

Time Slot Length - 15 (Minutes)

month  week  day   Feb 14 - 20, 2021              today   ‹  ›

|       | Sun 2/14 | Mon 2/15 | Tue 2/16 | Wed 2/17 | Thu 2/18 | Fri 2/19 | Sat 2/20 |
|-------|----------|----------|----------|----------|----------|----------|----------|
| 12pm  |          |          |          |          |          |          |          |
| 12:30pm |        |          |          |          |          |          |          |
| 1pm   |          |          |          |          |          |          |          |

Self Schedule or Patient Schedule?

Please select when the patient should schedule their next appointment.

Month ▾        Day ▾        Year ▾

Back   Schedule Now

Fig. 10D

Your appointment is pending approval...

Dear Paula:

We have notified Dr. Ben Carson that you are requesting an appointment. They must approve the appointment before it is confirmed. Once approved, a full appointment confirmation will be sent to you via email and text message.

If you have questions in regards to scheduling, please contact the practice directly.

Mend Demo

---

A new unapproved appointment has been scheduled...

Dear Dr. Ben Carson:

You have a new unapproved appointment scheduled for Thursday, April 18 at 12:30 PM EDT. Please login to the Mend Portal to approve or reschedule.

Mend Demo

Thursday, April 18 at 12:30 PM EDT

Basic Information

| | |
|---|---|
| Appointment Type | New Patient Video Visit - 45 minutes |
| Provider | Sample, Sarah |
| Scheduled Start Date | 10/04/2019 12:00 pm |
| Scheduled End Date | 10/04/2019 12:30 pm |
| Check In | |
| Symptoms | Cough, fever for two days |

Cancel　　　　Save

If you are unable to attend this appointment at the scheduled date and time, please cancel or reschedule your appointment: Modify Appointment

Appointment Information

| | |
|---|---|
| Type | Therapy New Patient Video Visit |
| Scheduled Start Date | 10/02/2019 11:15 am |
| Scheduled End Date | 10/02/2019 12:15 pm |
| Requested Start Date | 10/03/2019 12:00 pm |
| Requested End Date | 10/03/2019 01:00 pm |
| Confirmed Date | Patient has not confirmed appointment. |
| Last Connection Test Date | Patient has not tested. |
| Symptoms | No Symptoms Entered. |

Patient Reason

Conflict

[Approve] [Deny]

Please click the 'Select Patient' button and then select "Self" or "Dependent(s)"

Select Patient

Q Search

| Name ▲ | Dependents | Actions |
|---|---|---|
| Sample Sally | Child Sample | Select Patient ▼ |

- Self
- Dependent(s)
- Edit

Enter the reason for your visit here.

SYSTEM AND METHOD FOR TRANSFERRING DATA

CROSS-REFERENCE TO RELATED APPLICATIONS

This application claims priority as a continuation of U.S. patent application Ser. No. 17/201,372, filed Mar. 15, 2021, entitled "SYSTEM AND METHOD FOR TRANSFERRING DATA, SCHEDULING APPOINTMENTS, AND CONDUCTING CONFERENCES," which claims priority as a continuation-in-part of U.S. patent application Ser. No. 16/993,564, filed Aug. 14, 2020, entitled "PROCESS FOR COLLECTING ELECTRONIC PROTECTED HEALTH INFORMATION WITHOUT A LOGIN," which claims priority as a continuation of U.S. patent application Ser. No. 15/923,333, filed Mar. 16, 2018, entitled "PROCESS FOR COLLECTING ELECTRONIC PROTECTED HEALTH INFORMATION WITHOUT A LOGIN," which claims priority to U.S. Provisional Patent Application No. 62/472,927, filed on Mar. 17, 2017, entitled "PROCESS FOR COLLECTING ELECTRONIC PROTECTED HEALTH INFORMATION WITHOUT A LOGIN," the entire contents of which are hereby incorporated by reference.

BACKGROUND

The health care system needs to collect information from patients, providers, and others in order to function. This information is frequently of a sensitive nature, so sufficient security precautions must be taken to safeguard the information and comply with government regulations. For example, such systems must comply with the requirements of the Health Insurance Portability and Accountability Act of 1996 ("HIPAA"), as well as the Health Information Technology for Economic and Clinical Health Act, enacted under Title XIII of the American Recovery and Reinvestment Act of 2009 ("HITECH").

However, security often must be balanced against accessibility. Very secure processes for collecting healthcare information may be inconvenient to patients or caregivers, and sufficiently onerous processes might be an obstacle to actually collecting healthcare information. Alternatively, such processes might be bypassed or worked around if the capability exists to do so, negating much of their security value.

SUMMARY

An efficient and secure process by which users may enter sensitive information into an electronic information system may be provided. When information is required from a user, the electronic information system may be configured to generate a unique access link (uniform resource locator, or URL) for that user. The link may be sent to the user via electronic communication, such as a text message or email. When the user follows the link with a web browser, the system prompts the user to enter an additional piece of personal information that is not known to the general public. (Certain examples of this additional piece of information may include, for example, a video connection in which the user's physical appearance may be verified or an audio connection in which a voice recognition system may verify the user's voice, or alternatively may include a medical history, a clinical assessment, a survey, a photo, a PDF document or any other electronic document, payment information such as credit card information, or any other information or agreements such as may be desired. According to some exemplary embodiments, a portion of a document or piece of information, such as a portion of a medical history or even a single line item in the medical history, or a combination of documents or pieces of information—or a combination of portions—may be used instead.) Once identity is verified, the user may be required to electronically sign agreements. The user is then prompted to enter the required information.

Such a system may, by design, permit a user to enter information without requiring the user to enter a username and password. If the user accesses the system in such a manner, without entering a username and password, the user may be given access in a "no-login" state.

In the "no-login" state, the user may not have access to any protected health information. This means that the user may not be provided with any information by following the unique link. (However, in an exemplary embodiment, the user may thereafter be able to provide a username and password, or other information, to gain access to a "login" state.)

In the "no-login" state, the user may be able to push data into the system. However, as discussed, the user may be "firewalled" from doing anything else. This may be analogized to a bank deposit, wherein a user may be able to deposit funds in the bank account of another (or a bank account for which they have not provided appropriate credentials) but may be firewalled from withdrawing money from the account or otherwise accessing its funds.

In an exemplary embodiment, such a process for collecting electronic protected health information without a login may comply with security recommendations regarding two-factor authentication. Although a login and password may not be required to deposit information, a sufficient level of security may be achieved because two factors are required to submit information: something the user has (the unique link) and something the user knows (personally identifying information).

In an exemplary embodiment, the system may be configured to comply with HIPAA/HITECH regulations because it does not expose protected health information (PHI) of any kind. The user may opt to submit the requested information, and it may be entered without requiring all of the information stored for the user to be exposed.

According to an exemplary embodiment, a system for providing an efficient and secure interface for transferring protected electronic information may be configured to perform the following steps. First, the system may generate and send, from a server, to a user address, a unique access link, the unique access link comprising a uniform resource locator (URL) directed to a transfer login page, the transfer login page being a web page permitting uploading of protected electronic information and denying access to protected electronic information. (In an exemplary embodiment, the user may have already created a user account prior to this stage.) The system may then receive a request, from a user device, to access the transfer login page, and obtain, from the user device, a personal identifier. This personal identifier may be, for example, a record of the user (such as, for example, a date of birth of the user), some physical attribute of the user (such as a user's personal photograph), or some other record such as may be desired. The system may then verify the personal identifier, and, when the personal identifier is verified, grant the user device access to the transfer login page.

The system may also provide a full login page separate from the transfer login page, wherein the full login page is a web page permitting uploading of protected electronic information and permitting access to protected electronic information. At this point, the system may receive a request, from the user device, to access the full login page, and obtain, from the user device, user login credentials distinct from the personal identifier, such as password information. These user login credentials may then be verified, and, when the login credentials are verified, the system may grant the user device access to the full login page.

In an exemplary embodiment, an access link may be provided to the full login page on the transfer page. This may be, for example, a password entry field where the user can provide their full credentials.

In an exemplary embodiment, the system may include a secure application (such as a secure application running on a mobile device of the user) which may be used to verify the existence of one or more records or other subjects of photography. For example, according to an exemplary embodiment, a user may need to take a photo of themselves with the secure application, or a photo of some record. Alternatively, the personal identifier can be any other record or identifying information such as may be desired.

In some exemplary embodiments, it may be verified that the user is one that has consented to use the service, or it may otherwise be requested that the user sign one or more agreements before using the service. In such embodiments, an electronic signature may be collected from the user.

In some exemplary embodiments, the system may be used to establish at least one of a real-time audio or video connection.

In some exemplary embodiments, the system may instead be implemented on a kiosk. In such embodiments, it may be desired to have the user input other information (such as a separate password or PIN) in lieu of having the user select a unique link. In an exemplary embodiment, a kiosk may also be used to take audio or video data, such as a photograph if desired. In some embodiments, an administrator may monitor the user's activity on the kiosk, and may be able to cut off the user's access; in other embodiments, the user's access may be terminated after a certain time period or after the user has been inactive for some time.

BRIEF DESCRIPTION OF THE FIGURES

Advantages of embodiments of the present invention will be apparent from the following detailed description of the exemplary embodiments thereof, which description should be considered in conjunction with the accompanying drawings in which like numerals indicate like elements, in which:

FIG. 6B is an exemplary scheduling interface.
FIG. 6C is an exemplary scheduling interface.
FIG. 7B is an exemplary scheduling interface.
FIG. 7C is an exemplary scheduling interface.
FIG. 7F is an exemplary scheduling interface.
FIG. 8E is an exemplary scheduling interface.
FIG. 9A is an exemplary scheduling interface.
FIG. 9B is an exemplary scheduling interface.
FIG. 10C is an exemplary scheduling interface.
FIG. 10D is an exemplary scheduling interface.
FIG. 11A is an exemplary scheduling interface.
FIG. 11C is an exemplary scheduling interface.
FIG. 11D is an exemplary scheduling interface.
FIG. 11E is an exemplary scheduling interface.
FIG. 11F is an exemplary scheduling interface.
FIG. 12A is an exemplary scheduling interface.
FIG. 12B is an exemplary scheduling interface.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Further, many embodiments are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, these sequence of actions described herein can be considered to be embodied entirely within any form of computer readable storage medium having stored therein a corresponding set of computer instructions that upon execution would cause an associated processor to perform the functionality described herein. Thus, the various aspects of the invention may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

According to an exemplary embodiment, and referring generally to the Figures, various exemplary implementations of a process for collecting electronic protected health information without a login may be disclosed.

Figure 1:
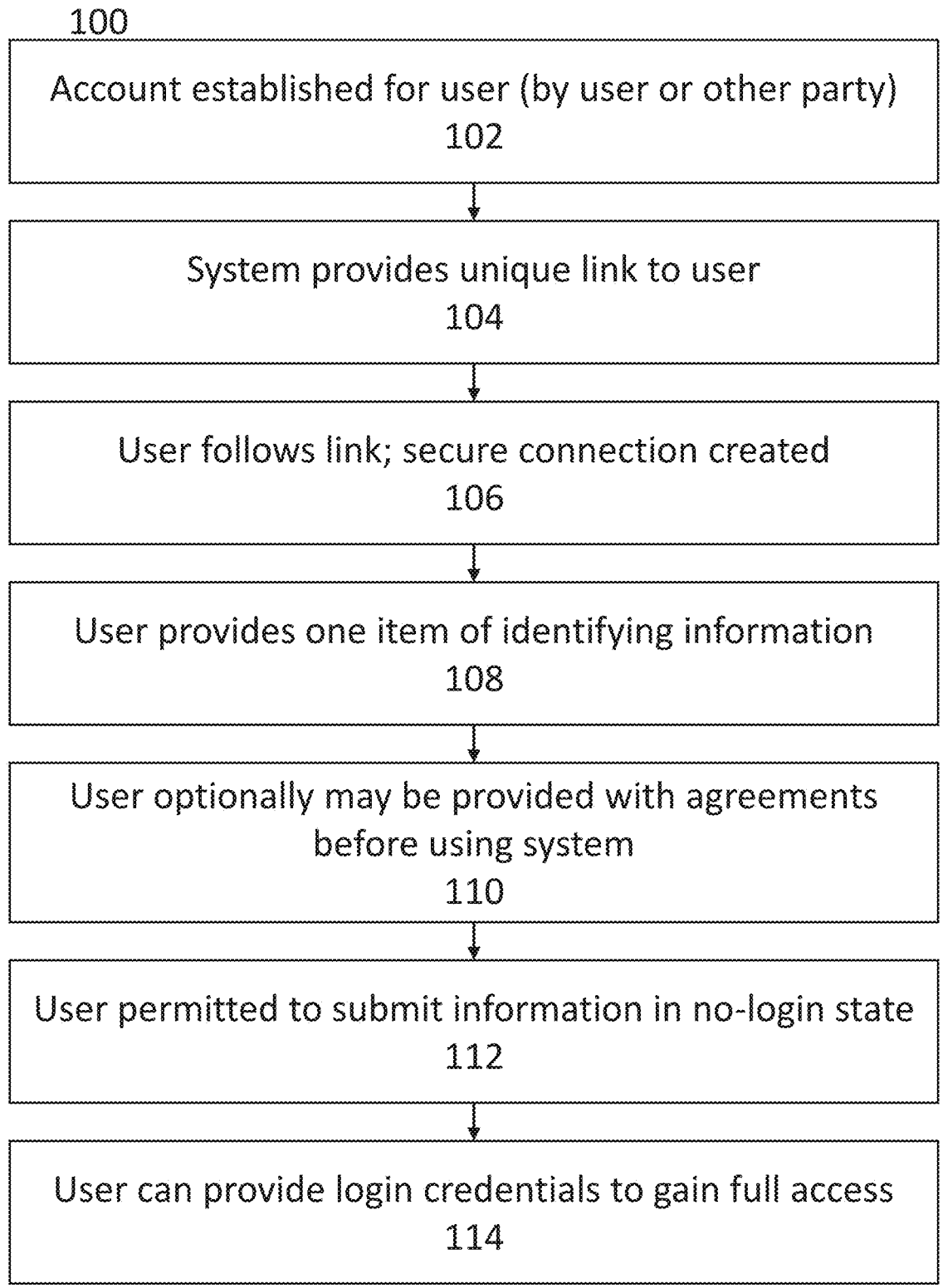
FIG. 1 is an exemplary flowchart depicting an exemplary embodiment of a process for collecting electronic protected health information without a login.

Turning now to exemplary FIG. 1, FIG. 1 displays an exemplary flowchart depicting an exemplary embodiment of a process for collecting electronic protected health information without a login 100.

In a first step 102, a user may establish an account, or an account may otherwise be established for a user. According to some exemplary embodiments, a variety of ways for an account to be established for a user may be contemplated; for example, according to some exemplary embodiments, a staff member with certain permissions may be able to make an account for a user or may be required to create or approve an account for a user. In another exemplary embodiment, an account may be created for a user by importing it from another service or by exporting it from the other service to the present service; in some exemplary embodiments, a user (or other party such as a staff member with permission to import data) may have the option to adjust certain information as necessary, such as the user's name if the user wants to use a different form of their name (such as a full legal name) that they were not using in the other account, or different payment information or contact information, or any other information such as may be desired. Alternatively, an account created for another service or for another organization may be automatically linked to the present account without requiring an import or export step. The establishment of such an account may require the user to enter a minimum set of personally identifiable information into the system. This may include one or more somewhat obscure items of personal information that may be used as the basis for identifying a user later on; for example, in an exemplary embodiment, a system may solicit a user's middle name, maiden name, or date of birth for such a purpose.

According to an exemplary embodiment, the system may be designed for use by any of patients, health care providers, staff members at a health care facility, or outside contractors. In an exemplary embodiment, a user may be a member of any such group. In an exemplary embodiment, the user experience provided to some groups may be different from that of some other groups; for example, it may be desirable to provide a somewhat higher level of security for submitting information when the user is a healthcare professional than when the user is a patient, and as such healthcare professionals may be requested to provide multiple items of information in order to access a no-login state. In some exemplary embodiments, the user permissions provided to a member of any one such group may be different from the user permissions provided to a member of another such group; for example, according to some exemplary embodiments, account creation privileges may be restricted to, for example, certain staff members at a health care facility or certain health cate providers, while patients or outside contractors may still be able to use the system once an account has been established for them.

In a next step 104, the system may provide a unique link, such as a uniform resource locator (URL) link, to a user. In an exemplary embodiment, such a link may be provided by email, by text message, or by another acceptable method for electronic communication, as may be desired. In some embodiments, user may be able to customize their electronic communication preferences; for example, a vision-impaired patient may request that the link be read to them in a telephone call.

According to an exemplary embodiment, a link may expire after a time interval. In an exemplary embodiment, this may be a predefined time interval, or may be a customized time interval; for example, a first form of communication may have a first time interval associated with it, and a second form of communication may have a second time interval associated with it, such that a user who receives a link via email has a longer or shorter time to access the link.

In some exemplary embodiments, links may expire by other methods instead of, or in addition to, time interval-based expiration. For example, according to an exemplary embodiment, a link may expire after it has been followed a certain number of times. For example, in one exemplary embodiment, a link may expire after it has been followed once, or followed a predefined number of times. In another exemplary embodiment, a link may expire after it has been followed once (or multiple times) and used successfully by the user to access a no-login state and deposit information, and may not expire if it is followed but not used successfully by the user to access a no-login state and deposit information (such as, for example, if the user does not complete one or more agreements or does not deposit information). In some exemplary embodiments, links may have one or more other security properties associated with them, as may be desired. According to an exemplary embodiment, an expiration status of a link may depend on the account or the user privileges of the account, or may be set by an account with particular user privileges. For example, an on-site account such as a staff account may have additional privileges (for example, it may be able to authorize the creation of accounts for patients, or may be able to manage the importing of accounts from other organizations or perform other management of accounts) and it thus may be desired to ensure that the account creation process for a staff member has additional security (for example, a link may expire in a very short period of time or after a single use, after which the staff member may have to request a new link) as compared to the account creation process for a patient (which may be more lenient, may allow for multiple account creation attempts and may expire only when an account is verified as being successfully created). Other embodiments may also be contemplated and may be implemented as desired.

In a next step 106, when a user has received a unique link, the user may access the unique link by a properly-equipped device, which may create a secure, encrypted connection between a web browser of the user and the system. According to an exemplary embodiment, one or more industry-standard encryption standards, such as SSL or TLS, or another form of encryption may be used in order to secure the connection.

In a next step 108, the user may be solicited for one or more pieces of identifying information. In an exemplary embodiment, this piece of information may be selected from the records of the user, and may be, for example, a user's date of birth. In another exemplary embodiment, the piece of information may be a piece of information specified by a user as an answer to a security question, or may be another password or passphrase (which may permit the use of a smaller password or passphrase than would otherwise be used, or may permit the use of a password or passphrase that the user is not asked to regularly update).

In a next step 110, the system may optionally prompt the user with one or more agreements that the user may be required to agree to before using the system. (In other exemplary embodiments, this may not be required, or may even be required at a different step; for example, it may be contemplated that users may be reminded of the agreements any time they attempt to use the system, and as a result the users may be provided with the agreements at an early step in the process, before they have signed in and regardless of whether they have already signed the agreements or not.) In an exemplary embodiment, a user may be asked to electronically sign the agreements before they are granted permission to use the system. In an exemplary embodiment, such agreements may be presented and archived in a manner that specifically complies with government regulations, for example the federal ESIGN act.

In a next step 112, a user may be permitted to submit information in the no-login state. For example, according to an exemplary embodiment, a user may be permitted to submit one or more forms, photos, documents, or any other type of information. In another exemplary embodiment, a user may submit photos of a driver's license or other forms of identity. In another exemplary embodiment, a user may submit payment information. In another exemplary embodiment, a user may submit health insurance information, or other information that may be related to reimbursement for care. In another exemplary embodiment, a user may submit any other piece of information that may be necessary to provide, facilitate, monitor, or transition care.

In an exemplary embodiment, the system may establish or may have the option of establishing a real-time audio, video, or audio/video session between the user's system and one or more other systems. This may operate to connect one or more patients to one or more health care professionals or anyone else involved in the care delivery process.

In an exemplary embodiment, the system may include a dedicated application provided to the user through which the user may be permitted or may be required to submit one or more items of information. In some exemplary embodiments, such an application may be analogous to a mobile banking application and may offer similar capabilities. For example, according to an exemplary embodiment, a user may be required to use a smartphone application to take a photograph of the one or more forms of identity of the user (such as the user's driver's license) rather than permitting the user to upload a photograph. This may ensure that the photos are current photos, and that the photos are not stored on the device and are properly encrypted when transmitted.

In an exemplary embodiment, a user may at any time be able to provide credentials in order to gain full access 114. In another embodiment, a first system may permit the deposit of information in a "no-login" state, and a separate second system may permit the deposit and retrieval of information when a login is provided may be separate systems, which may function to provide additional security.

Figure 2:
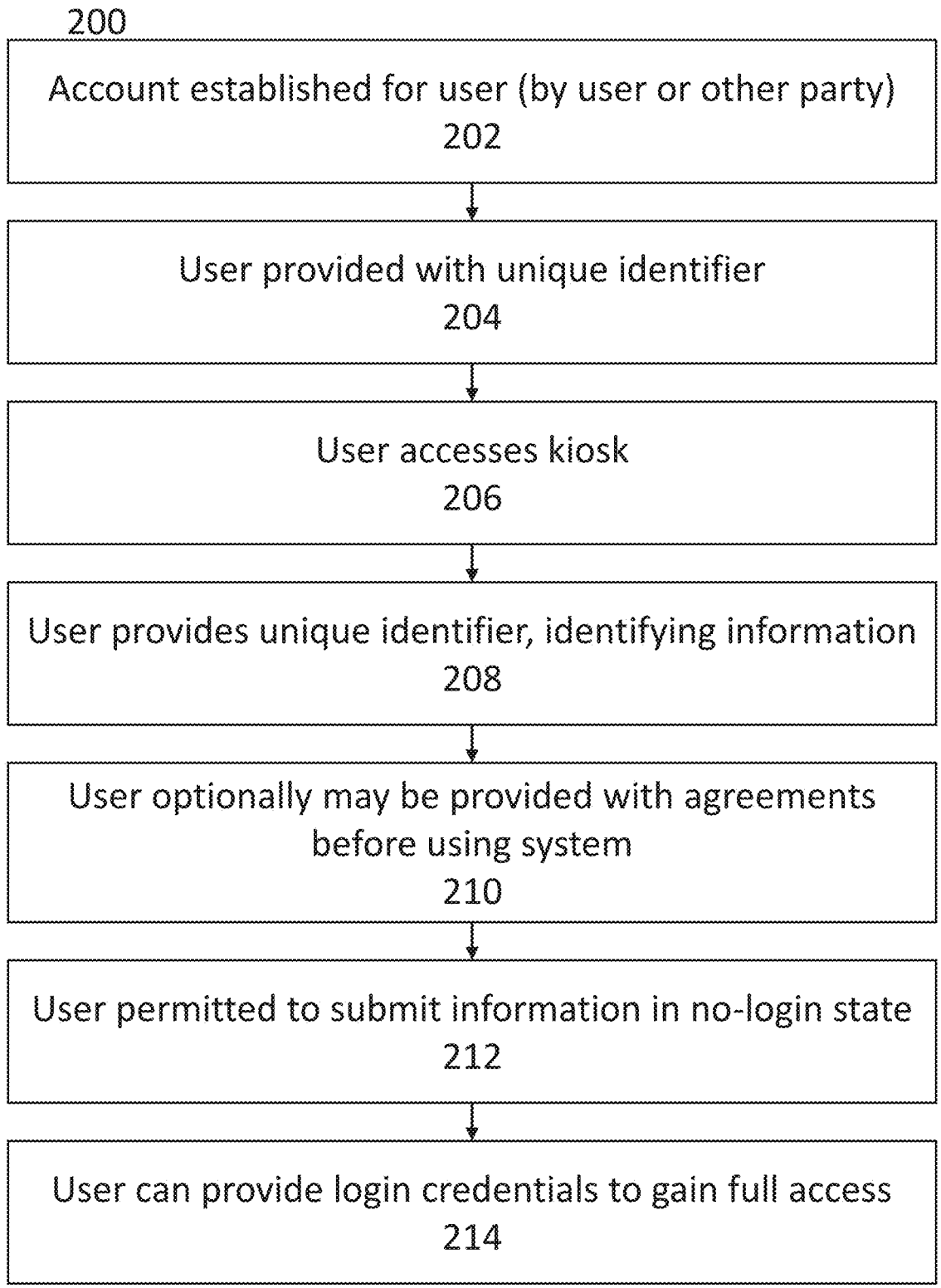
FIG. 2 is an exemplary flowchart depicting an exemplary embodiment of a process for collecting electronic protected health information without a login, in a "kiosk mode."

Turning now to exemplary FIG. 2, an alternative exemplary flowchart depicting an exemplary embodiment of a process for collecting electronic protected health information without a login 200 may be provided. Such an exemplary flowchart 200 may depict a "kiosk mode," wherein a user that is unable to access the information system from one of their own devices (or does not wish to access the information system from one of their own devices) may instead access the information system through a kiosk. According to an exemplary embodiment, a kiosk may be an interactive electronic device, such as a desktop or laptop computer, a tablet or mobile device, or another interactive device, as may be desired. In some exemplary embodiments, a kiosk may be a dedicated device; for example, in some embodiments, a booth kiosk with a tablet dedicated to running the kiosk software may be provided. In other exemplary embodiments, a device may be temporarily reconfigured into a kiosk mode by running appropriate software. A kiosk may be provided in and maintained in a facility of a provider, which may be, for example, an office, clinic, or hospital, or may be provided in another accessible location. This may facilitate information entry by patients who lack access to technology, ensuring that patients without such access (for example, patients that cannot afford an appropriate device, or patients that were taken to a hospital without their device, or any other such patients) can still make use of the information system.

According to an exemplary embodiment, a user may establish an account or may have an account established for them 202. (As noted above, according to some exemplary embodiments, there may be many ways in which this may be done; for example, in some exemplary embodiments, it may be contemplated that a staff member or other authorized user may create the account, may be contemplated that the account information may be imported from elsewhere or exported from another service to the present service, may be contemplated that the account may be shared with another service or otherwise created as part of a different service or on behalf of another organization, and so forth). The user may be provided with a unique identifier 204, which may be selectable by the user or may be provided to the user, which may be done contemporaneously with (or before or after) the user creates their account. This may be, for example, a PIN (such as a six-digit PIN) or may be other appropriate information.

A user then may access a kiosk 206 in order to deposit information. When the user attempts to access the kiosk 206, the user may be prompted to enter the unique identifier and their identifying information 208; in this way, the unique identifier may take the place of the unique link that would have been sent to the user had the user made use of another system. The user may then be provided with agreements before using the system 210 (which, again, as mentioned above, may be optionally moved to a different position in the method or may be optionally removed), may be able to submit information 212, and may optionally be able to login with full credentials 214.

Figure 3:
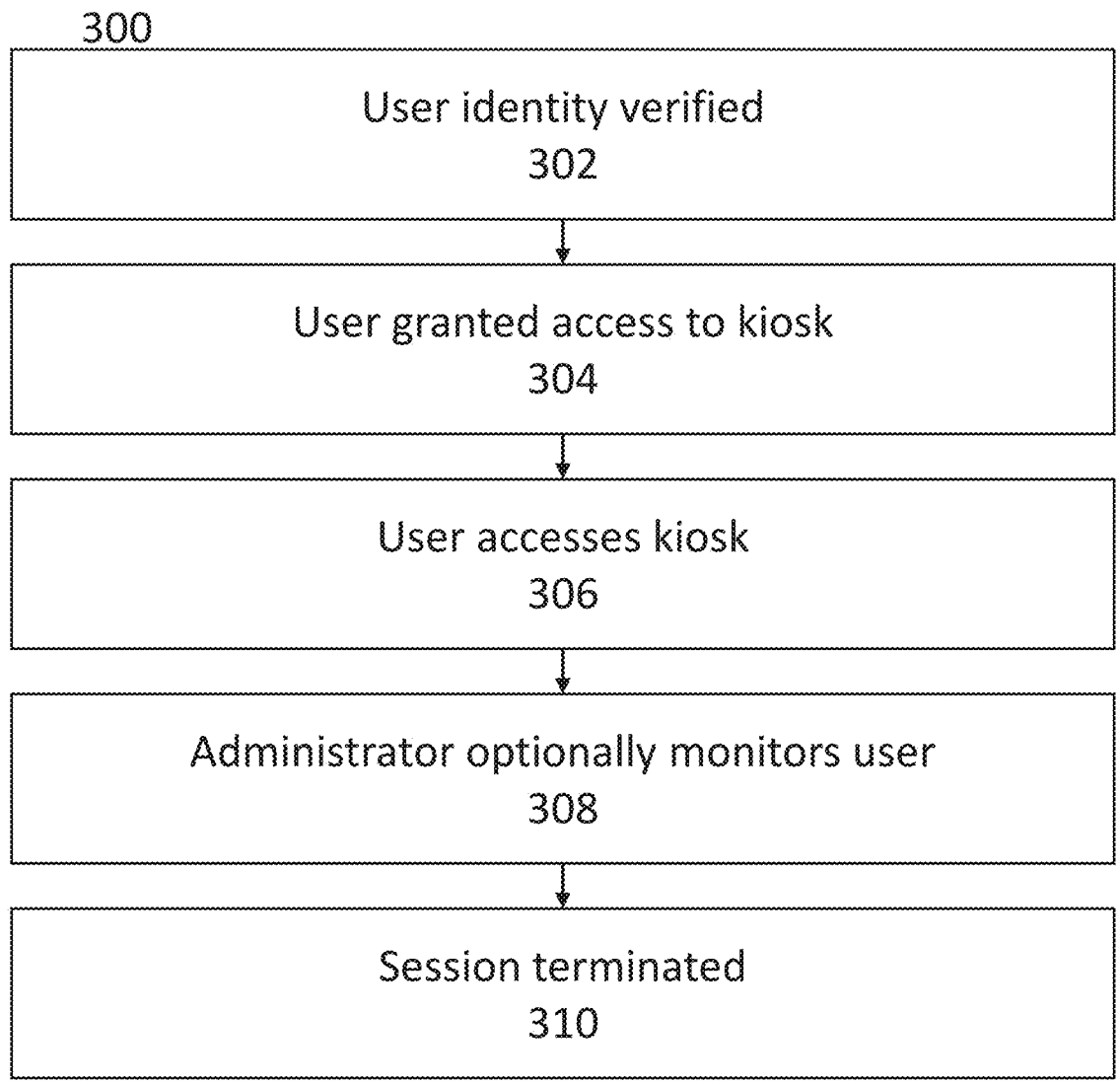
FIG. 3 is an exemplary flowchart depicting an exemplary embodiment of a process for collecting electronic protected health information without a login, in a "kiosk mode."

Turning now to exemplary FIG. 3, an alternative exemplary flowchart depicting an exemplary embodiment of a process for collecting electronic protected health information without a login 300 may be provided. Such an exemplary flowchart 300 may depict an alternative "kiosk mode."

According to an alternative embodiment of a "kiosk mode" 300, a user may not be provided a unique identifier before accessing the kiosk. Instead, the user—who may specifically be a user who is a patient—may not need to enter any information. Instead, one or more administrators of the kiosk (who may be, for example, hospital staff members) may verify the patient's identity, either personally or using a different utility. The administrator may then remotely trigger a device to provide access to the kiosk.

In an exemplary embodiment, the administrator may further trigger a device (for example, in the same operation as provision of access) to collect audio and/or video information from the kiosk. For example, if the user has initiated an audio and/or video connection on the kiosk, the user's audio and/or video connection may be provided to the administrator as well. The administrator then may be provided with remote functionality over the device so that they can monitor whether the user (for example, a patient) and the person that the user is connected to (for example, a healthcare provider) are both participating. In an embodiment, the administrator may be able to remotely end the session on the kiosk, for example if one or both of the user and the healthcare provider are not participating. (Alternatively, some or all of these processes may be automatic, such that a software service monitors whether the user or the other party is participating, based on attributes such as active call state information, a time period since either party last used the connection to make any sort of communication whatsoever, and so forth, such that the software service can automatically terminate the connection.) In an embodiment, the administrator may operate a dashboard that controls more than one kiosk; in an embodiment, an administrator may be able to assign device names and control many devices simultaneously from a single dashboard.

In the process depicted in exemplary FIG. 3, a user may have their identity verified 302. The user may then be granted access to a kiosk by an administrator 304, which they may then access 306. The administrator may monitor the user 308 during their session. (In some exemplary embodiments, this may be optional, and an administrator may have the option to monitor the user 308 during their session that they may choose not to exercise, or the step of monitoring the user 308 may be performed by a different service such as a software service or may not be performed at all.) The administrator may then opt to remotely end the session 310, for example by a control dashboard. (Alternatively, the session may be terminated 310 remotely, for example by a software service that determines when the session is over, such as by listening for particular keywords or by waiting for a sufficiently long period of inactivity. This may cause the session to automatically timeout or automatically finish and end, such as may be desired. Alternatively, users may end the session, such as may be desired.)

Figure 4:
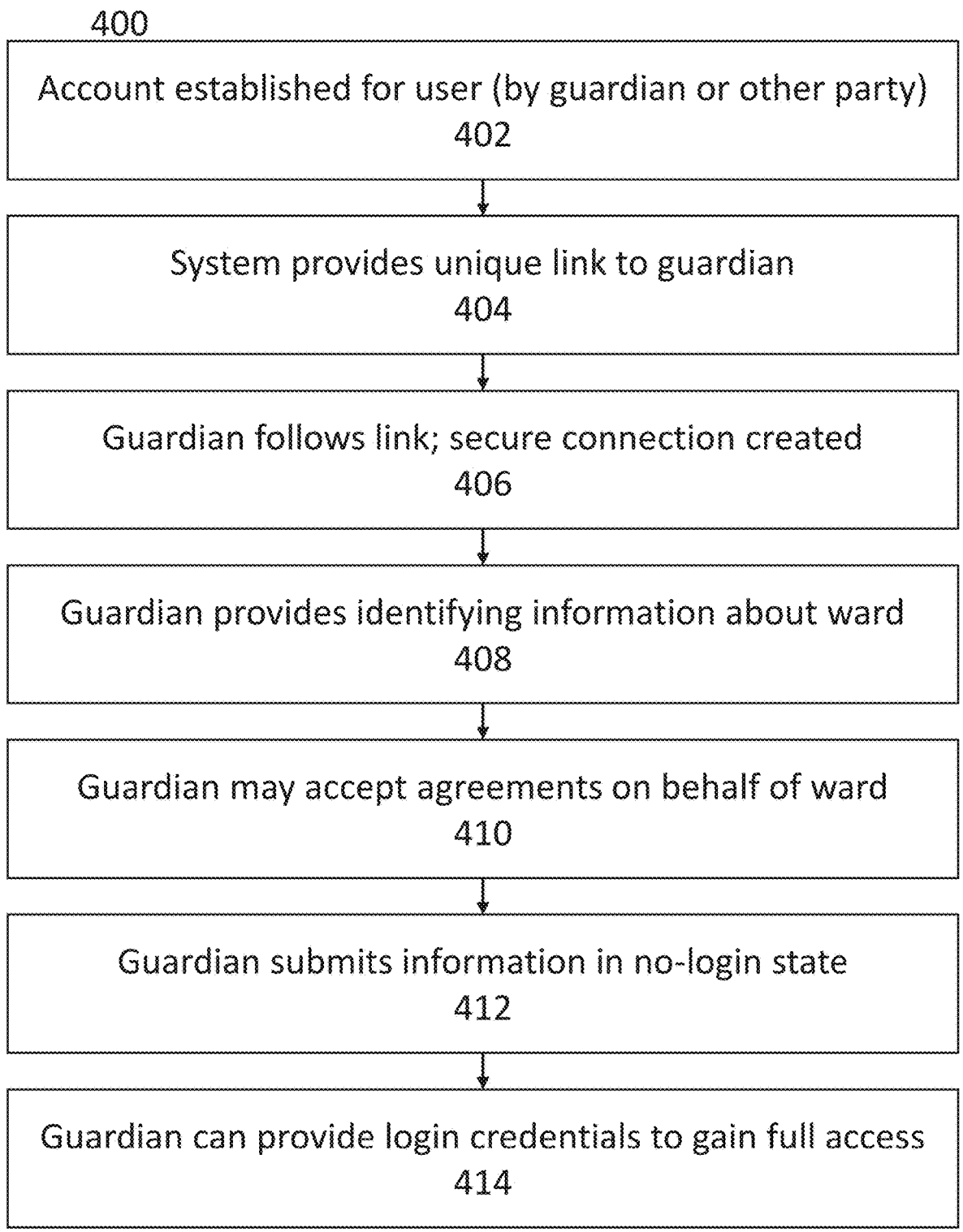
FIG. 4 is an exemplary flowchart depicting an exemplary embodiment of a process for collecting electronic protected health information from a first party on behalf of a second party without a login.

Turning now to exemplary FIG. 4, FIG. 4 displays an exemplary flowchart depicting an exemplary embodiment of a process for collecting electronic protected health information without a login 400 from a user unable to provide the information themselves.

According to an exemplary embodiment, it may be desired to empower a guardian, such as a guardian of a person under the age of consent, a person who is mentally incapacitated, or a person who is otherwise disabled, to deposit information on behalf of their ward. According to an exemplary embodiment, the guardian 402 may establish an account on behalf of the ward, or may take over an existing account (such as an account made by the ward before becoming physically or mentally incapacitated). (According to an exemplary embodiment, an account may also be established as contemplated in previous embodiments; for example, it may have to be created by an authorized staff member, or may be imported from another service or shared with another organization, and so on and so forth.) The system may then provide a unique link to the guardian 404 instead of to the ward. The guardian may then follow the link 406. The guardian may then enter some piece of information about the ward in order to verify the identity of the ward 408; according to an exemplary embodiment, in some cases, it may be desired to have the guardian enter a piece of information about the guardian instead. The guardian may then accept agreements on behalf of the ward 410 (if any agreements are to be accepted; this may depend on, for example, whether the system contemplates that any agreements need to be provided at all, as well as whether a ward has previously signed these agreements, and whether any new agreements need to be signed authorizing aspects peculiar to the guardianship embodiment). The guardian may then be able to submit information in a no-login state 412, and may be able to provide login credentials to gain full access 414, should this be desired.

Now referring generally to the Figures, one or more tasks may be completed before, during, or after the execution of any of the aforementioned processes. For example, according to an exemplary embodiment, a process may include connecting to or collecting data from any stakeholder in the process, which may include doctors, nurses, caregivers, counselors, case managers, or any other stakeholders, as may be desired. In an exemplary embodiment, one or more pieces of information may be collected; in some embodiments, what information is requested at any time may differ, such that each session is dynamic based on what is being requested from that particular stakeholder at a particular stage in the process.

In an exemplary embodiment, multiple layers of data may be collected in a single session, which may, for example, be maintained as a no-login session. For example, according to an exemplary embodiment, a user may sign into their account via a no-login method. The user may then be asked to sign consents and to complete one or more assessments. Following the completion of the consents and the assessments, the user may be connected to, or may have the option to connect to, a live audio/video session.

Now referring to exemplary FIGS. 5-12, an improved appointment scheduling system and process may be provided. The system may be used for service providers and organizations of all types and an exemplary embodiment described herein may be a healthcare provider embodiment. There may be multiple options for scheduling appointments of varying types. More specifically, scheduling system options may include an ad-hoc video scheduling, instant virtual exam room scheduling, single-page booking, or a full appointment scheduling process. One or more scheduling options may optionally be implemented simultaneously. The scheduling systems may create and send a video connection invitation to at least one of a mobile phone number, an email address, and a patient/user signed up to the appointment scheduling system platform through a webpage or mobile application. The scheduling systems may create an audio and/or a video conferencing session and invitation for immediate connection, a future time, or both. The scheduler and/or provider may initiate sending an invitation from a dashboard in the scheduling system and connect immediately to the video session. In other embodiments, the scheduler or provider may create a generic appointment on a dashboard of the system and may join the visit from the dashboard. In still other embodiments, the scheduler and/or provider may create an appointment using a dashboard in a calendar view and may select any provider, location, or appointment type. The scheduler and/or provider may then join the visit from the dashboard. According to further embodiments, the scheduler and/or provider may use an appointment selection triage to ensure the correct provider, location, and appointment type are chosen. The scheduler and/or provider may then join the visit from the dashboard. According to one or more of the scheduling system embodiments, the patient may receive a secure video link and join the visit instantly as an anonymous user; receive a secure video link (and reminders when applicable), verify identity with date of birth and/or create an account, and sign electronic consents when applicable before joining a visit; or receive appointment reminders, connection tests, and a secure video link, verify identify with date of birth, and sign electronic consents and/or complete intake forms when applicable. According to an exemplary embodiment, the organization optionally may not keep a record of the video session and may or may not track session metrics.

According to an exemplary embodiment, an ad-hoc video appointment scheduling system may be provided. The ad-hoc video scheduling system may provide scheduling for emergency telehealth treatment. The ad-hoc system may also be implemented as an appointment scheduling system for organizations that use Electronic Health Records (EHR) as a master schedule. The ad-hoc video scheduling system may utilize appointment invitations sent to a mobile phone number or an email address. Ad-hoc video scheduling may optionally set up for immediate appointments or appointments right now. Ad-hoc video scheduling may optionally allow for video connection scheduling only. In operation, the scheduler and/or provider may send an invitation from a system dashboard and may connect immediately to a video conference appointment. The user or patient may receive a secure video link and may join the visit using the link. The user or patient may join the video conference instantly upon clicking the link. The user or patient may join as an anonymous user. In some embodiments, the anonymous user status is required when joining instantly or when identity is not verified. According to an exemplary embodiment, the provider organization may not keep a record of the video session.

According to some exemplary embodiments, an ad-hoc video session may have restricted functionality. Ad-hoc sessions may optionally not require a patient account, not create an appointment record, not include full functionality within the video session (providers may not have access to patient details, appointment notes, follow-up booking, marking patients as a no-show, etc.), not include associated reporting, and not sync with EHR.

Figure 5A:
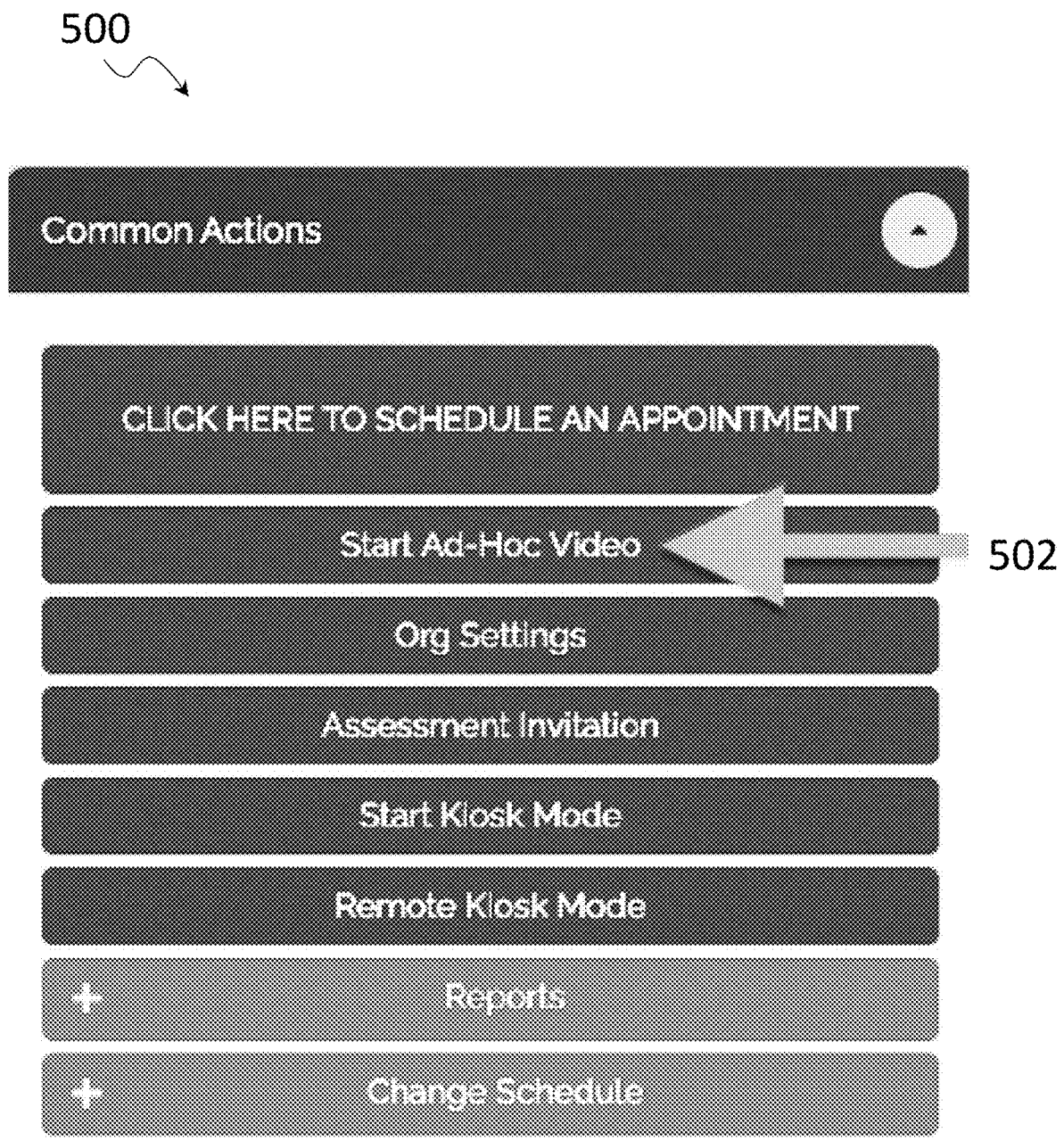
FIG. 5A is an exemplary scheduling interface.
Figure 5B:
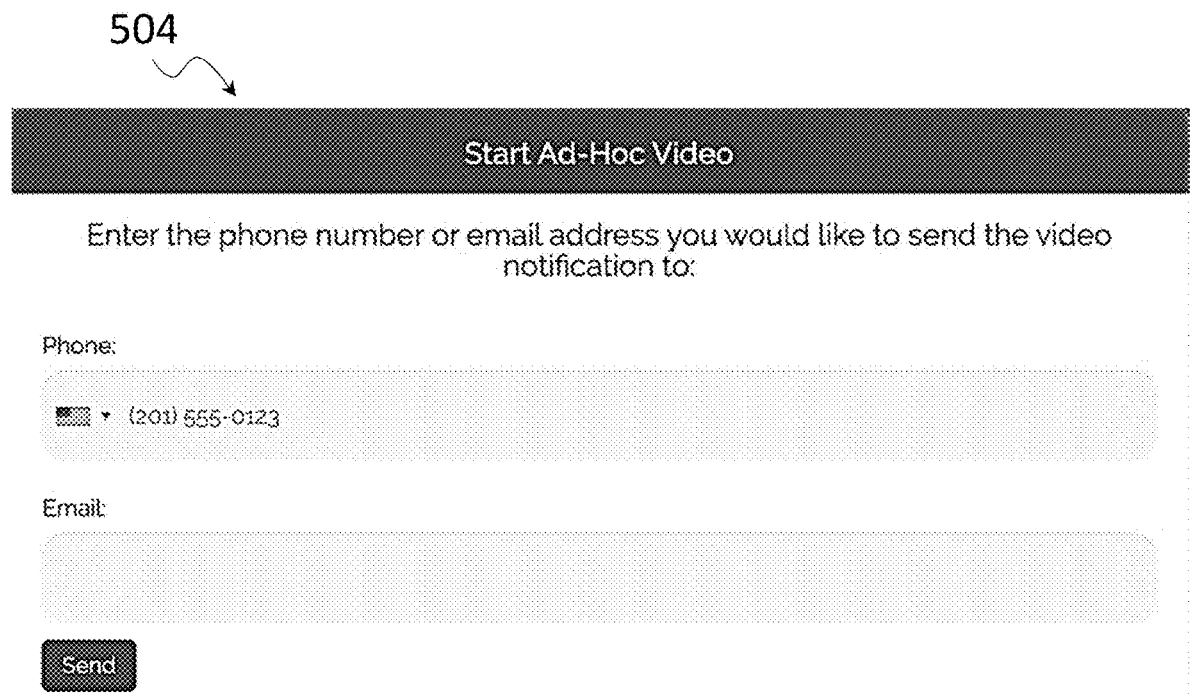
FIG. 5B is an exemplary scheduling interface.
Figure 5C:
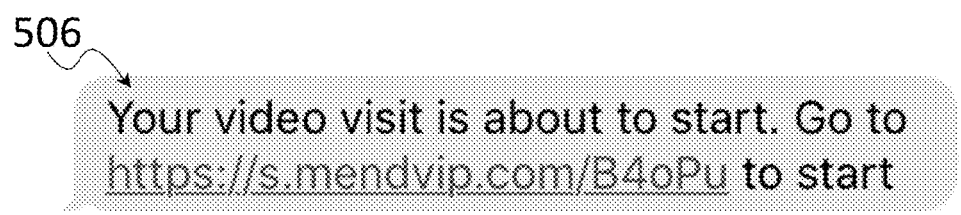
FIG. 5C is an exemplary scheduling interface.

As shown in exemplary FIG. 5A-5C, a Start Ad-Hoc Video button 502 may be presented on an organization or provider dashboard 500. When selected, a Start Ad-Hoc Video window 504 may open, which may optionally require entering a user or invitee's contact information, such as telephone number and/or email address. Once invitee contact information is provided, a unique and secure video link 506 may be sent to the invitee using the contact information, such as by SMS text message, email, or other forms of communication, as would be understood by a person having ordinary skill in the art. The link may also optionally be sent to a provider. Once a notification or video link has been sent, the provider may be automatically directed to a virtual waiting room. Once a user, invitee, or patient engages the notification and/or link, they may also be directed to the virtual waiting room, which may initiate the video conference once the parties have joined. According to some exemplary embodiments, the video session facilitated through the virtual waiting room may be initiated immediately, upon at least two parties joining, or once all parties have joined. To conclude or complete a session, a "hang up" or end-session button may be provided. As shown in the figures, the "hang up" button may be a button at the bottom of a virtual waiting room screen and may optionally be red. Upon ending a session, the provider may exit the virtual waiting room and may be automatically returned to a dashboard.

Figure 6A:
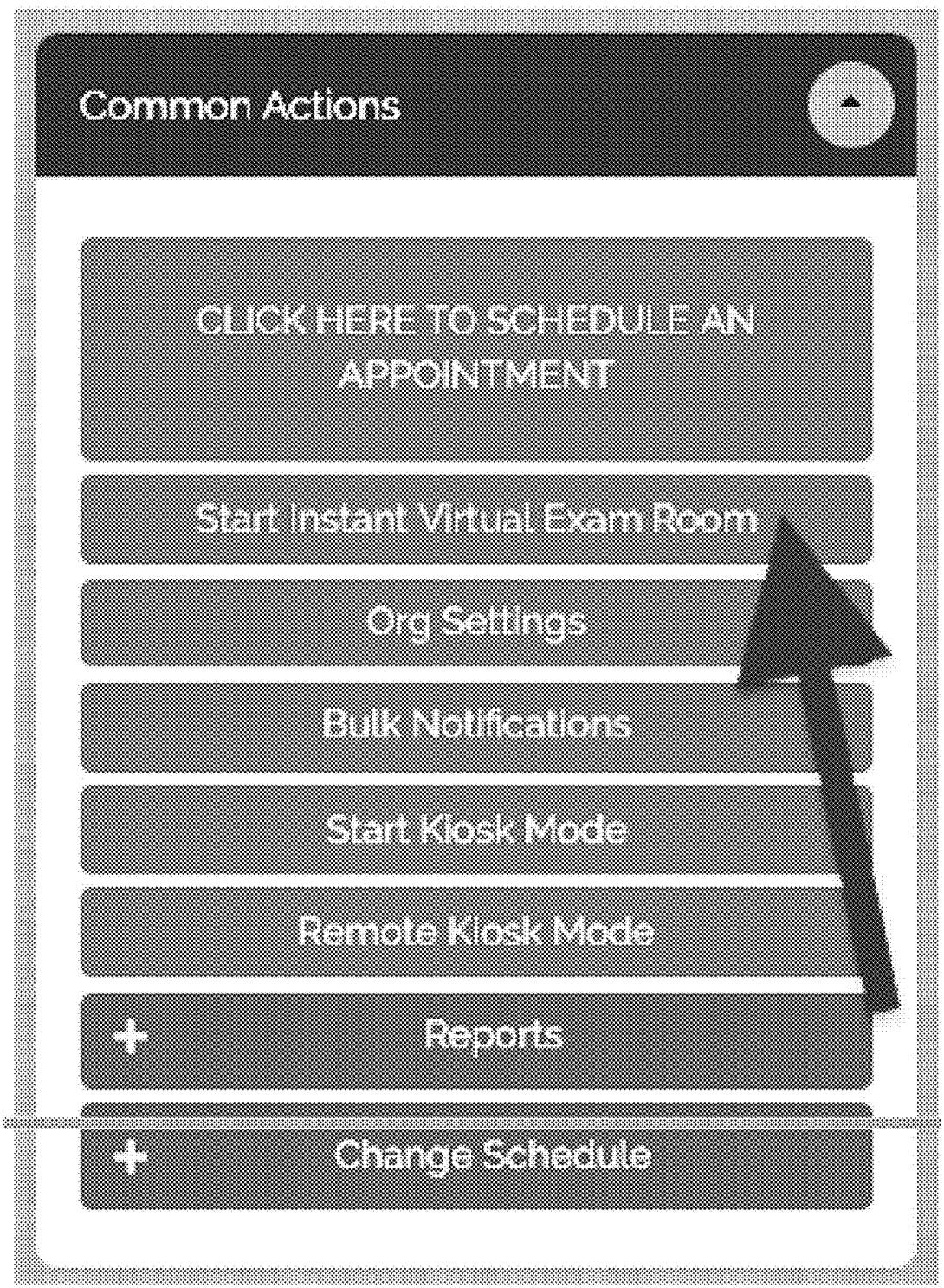
FIG. 6A is an exemplary scheduling interface.
Figure 7A:
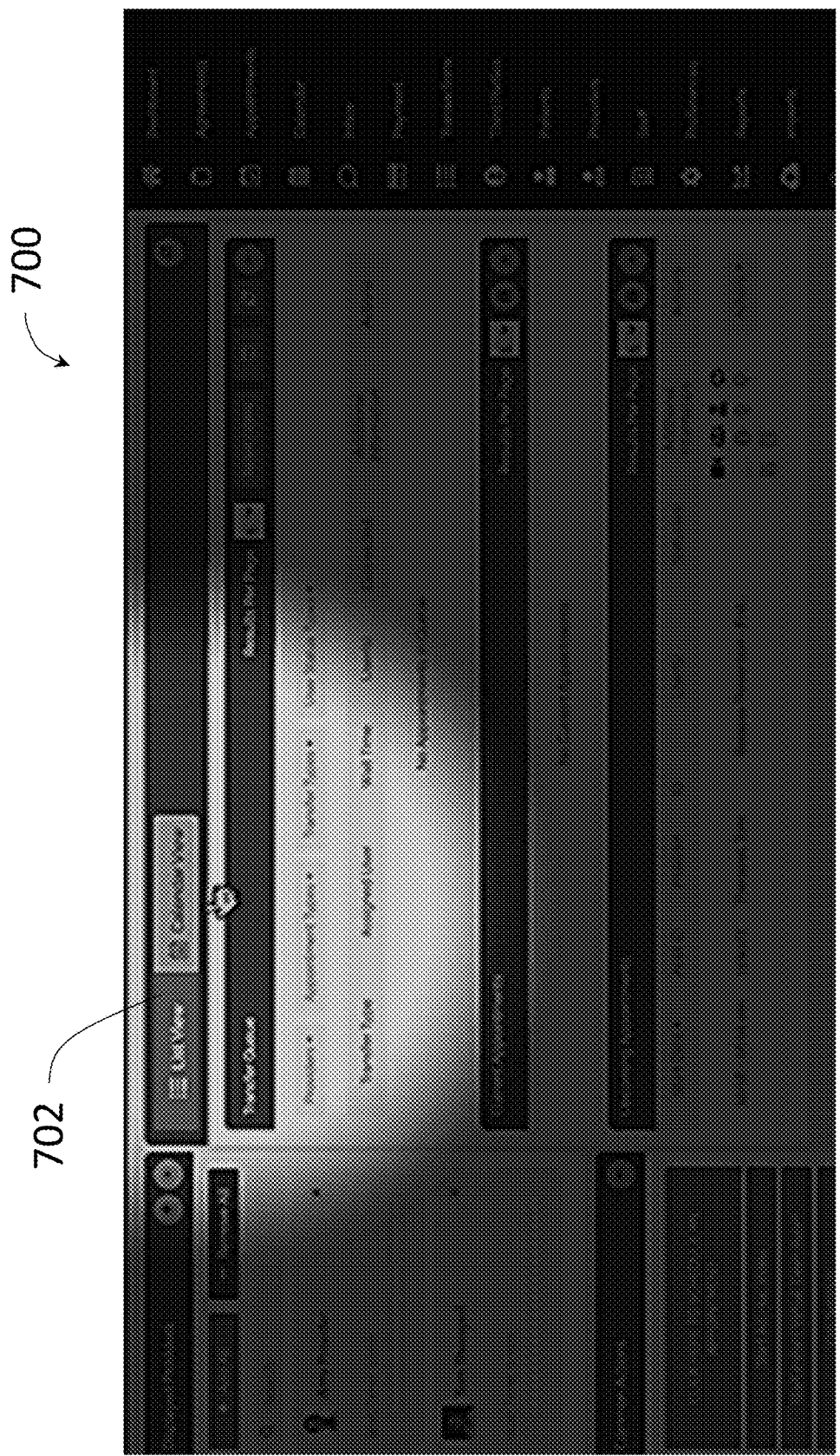
FIG. 7A is an exemplary scheduling interface.
Figure 7D:
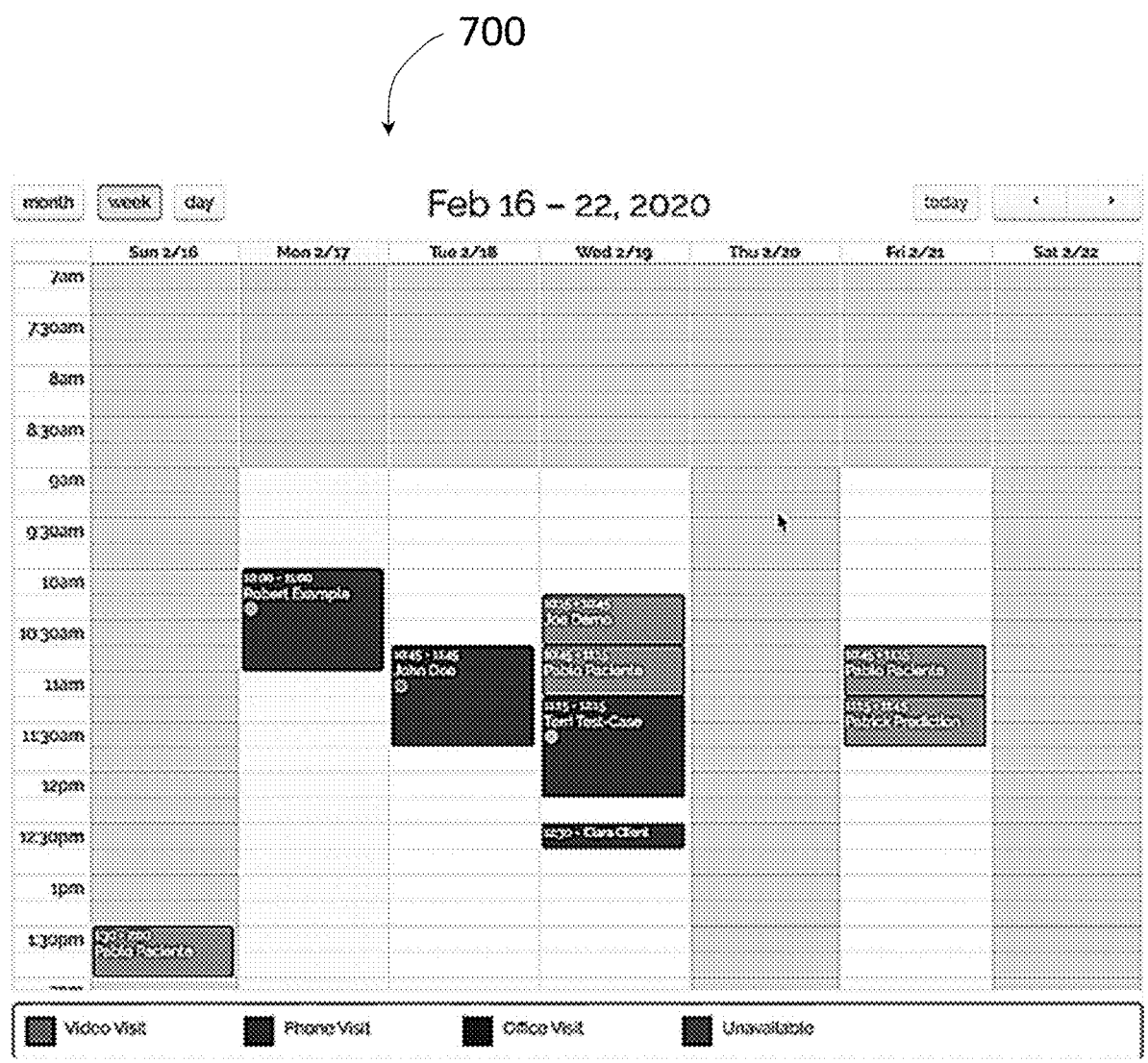
FIG. 7D is an exemplary scheduling interface.
Figure 7E:
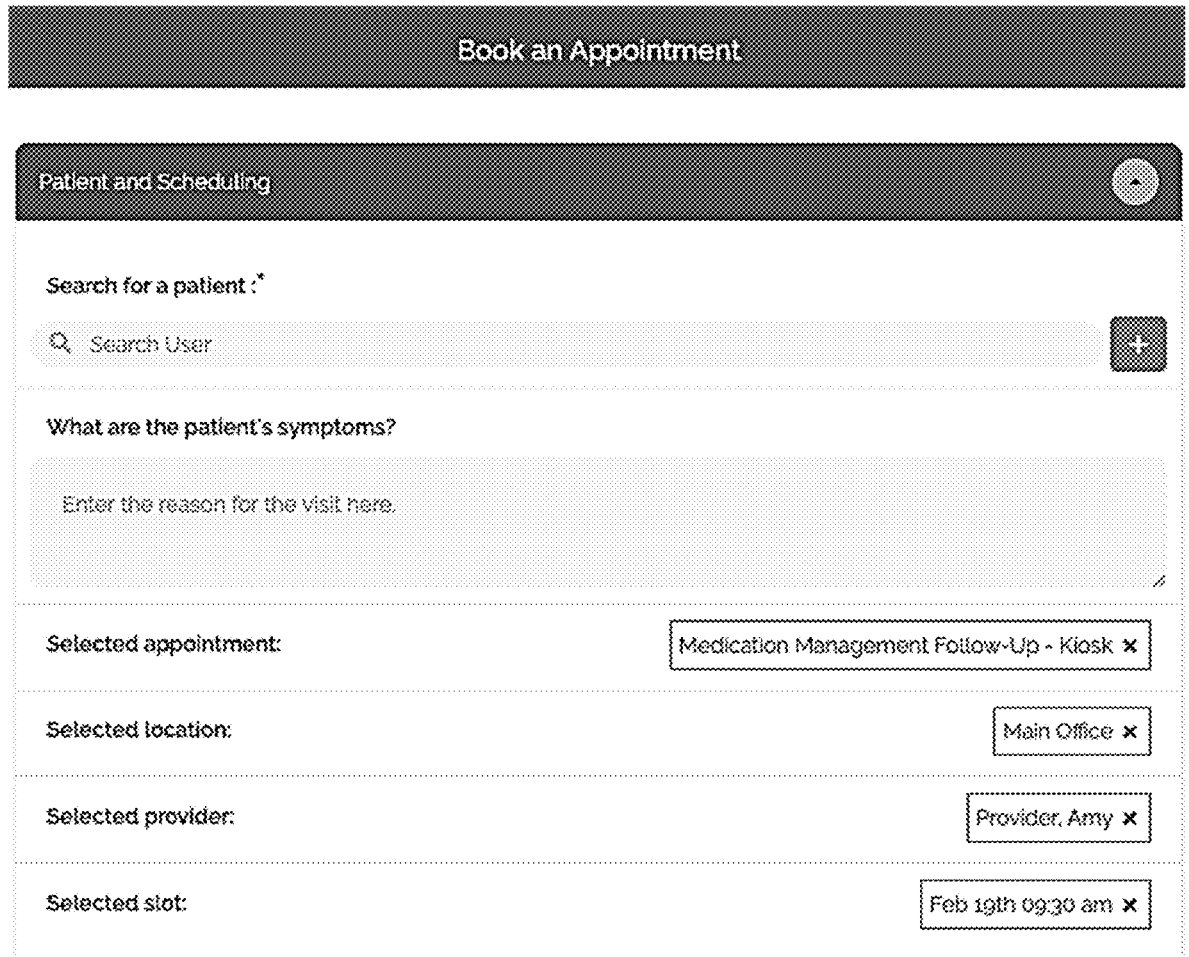
FIG. 7E is an exemplary scheduling interface.
Figure 8A:
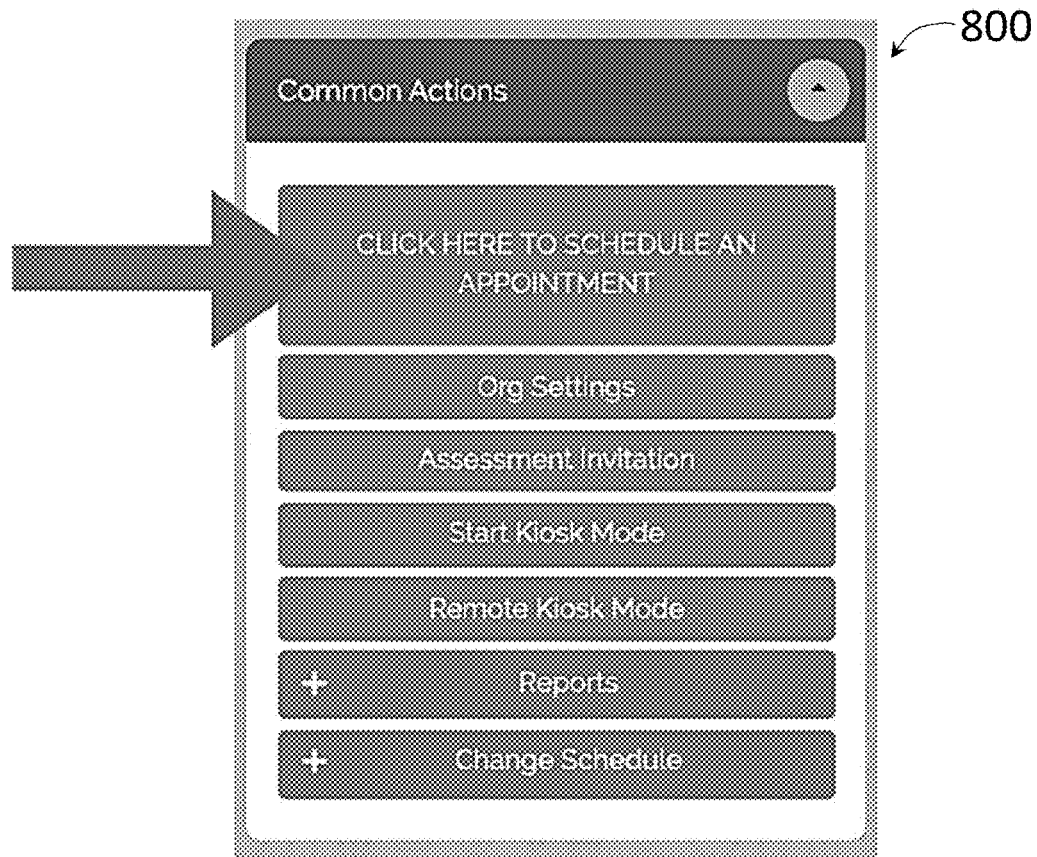
FIG. 8A is an exemplary scheduling interface.
Figure 8B:
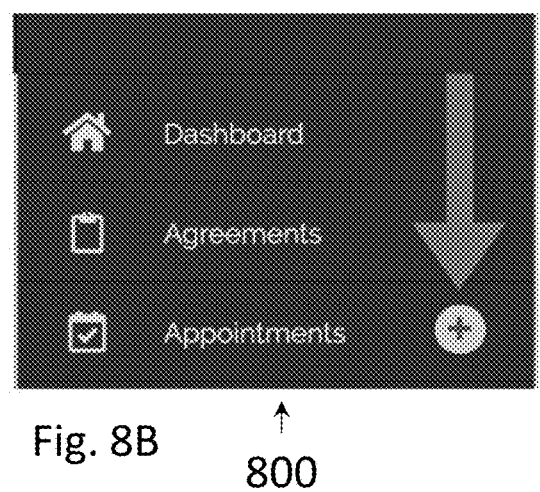
FIG. 8B is an exemplary scheduling interface.
Figure 8C:
FIG. 8C is an exemplary scheduling interface.
Figure 8D:
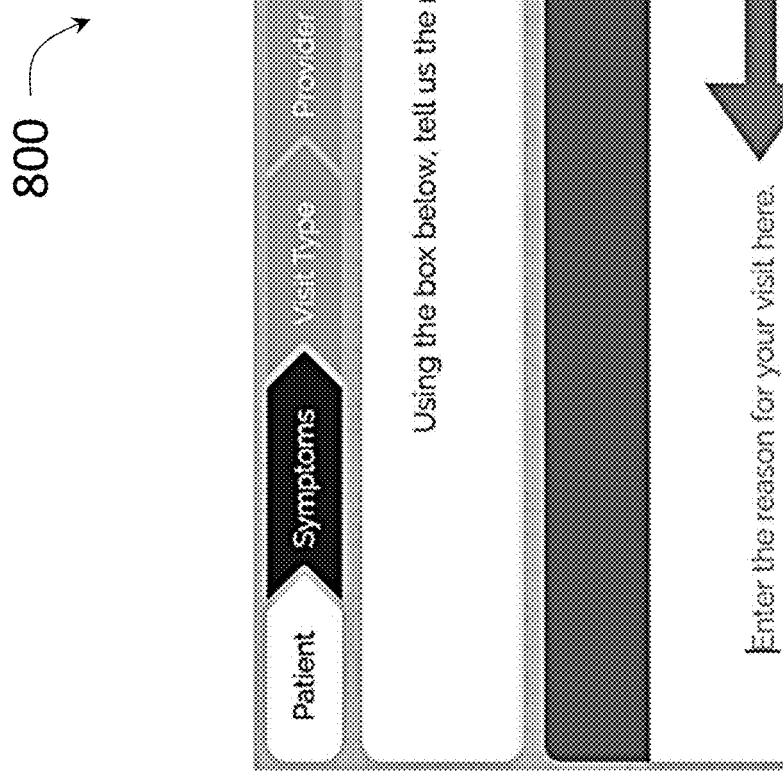
FIG. 8D is an exemplary scheduling interface.
Figure 8F:
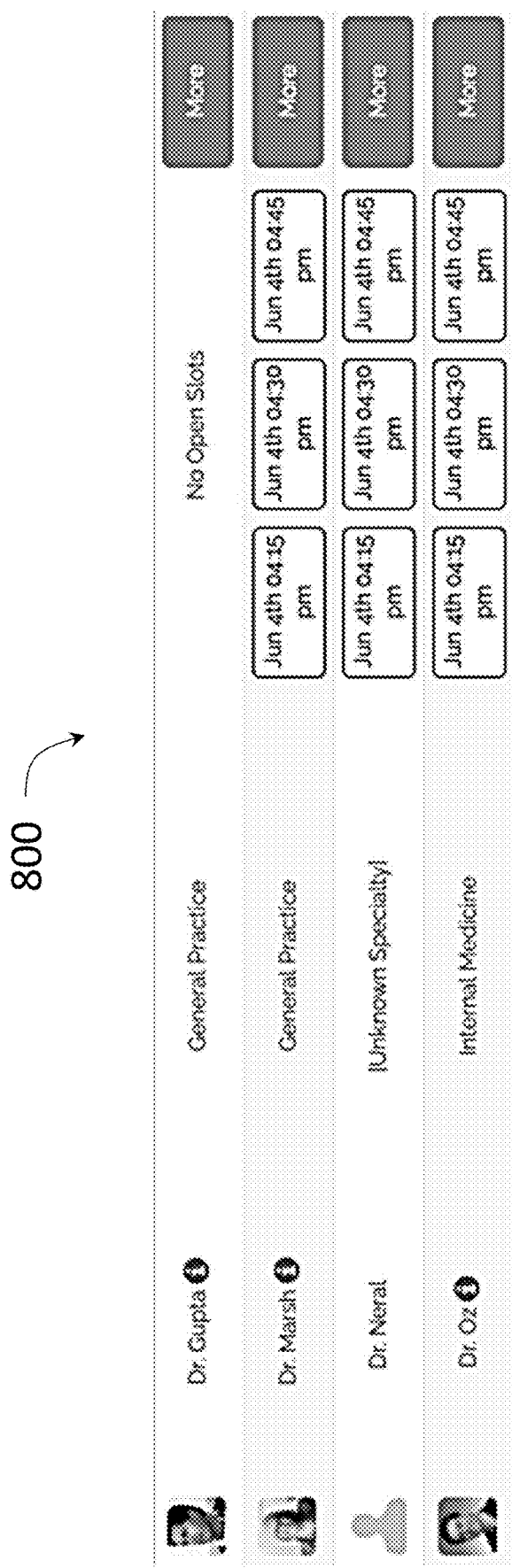
FIG. 8F is an exemplary scheduling interface.
Figure 8G:
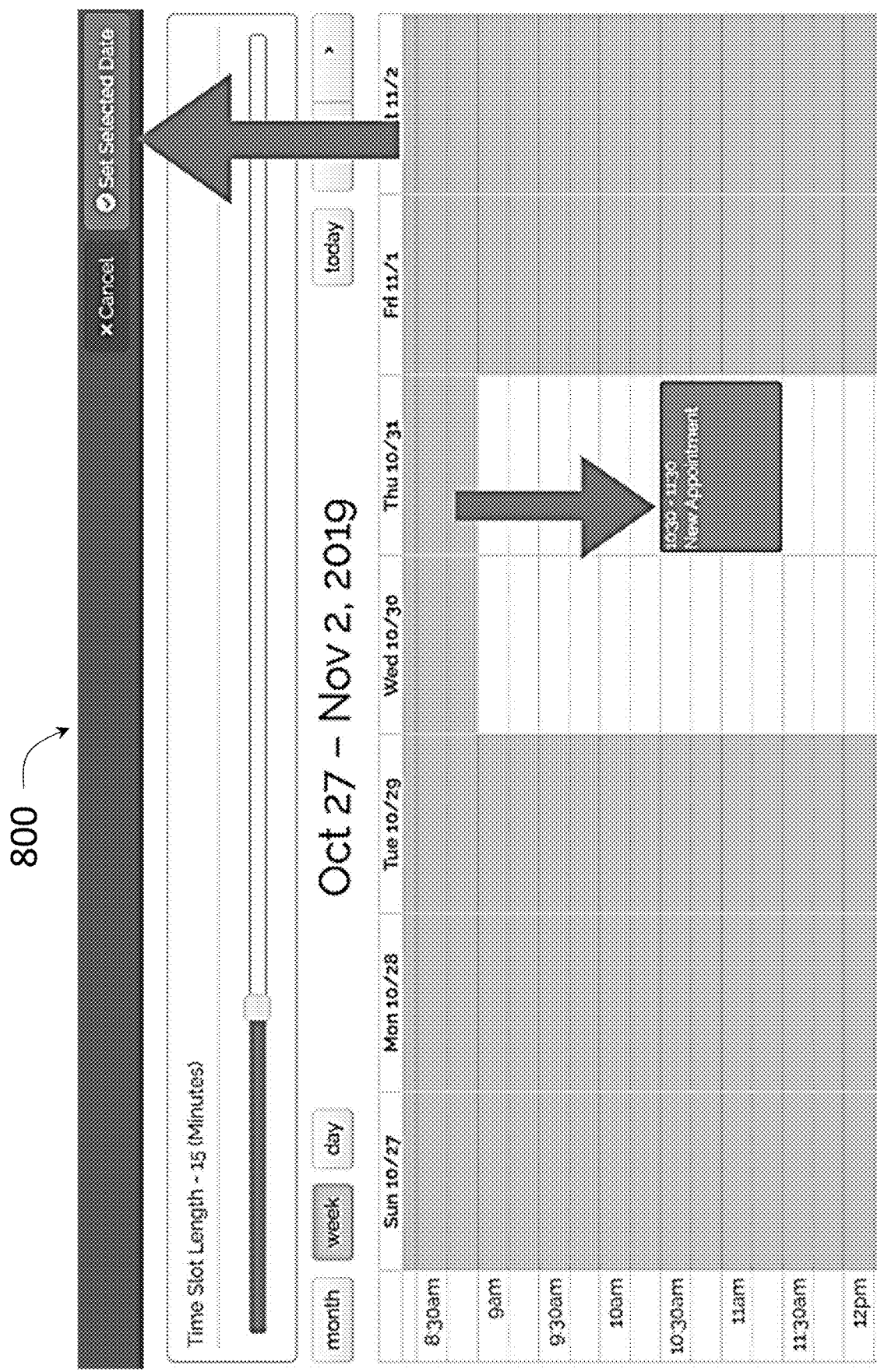
FIG. 8G is an exemplary scheduling interface.
Figure 8H:
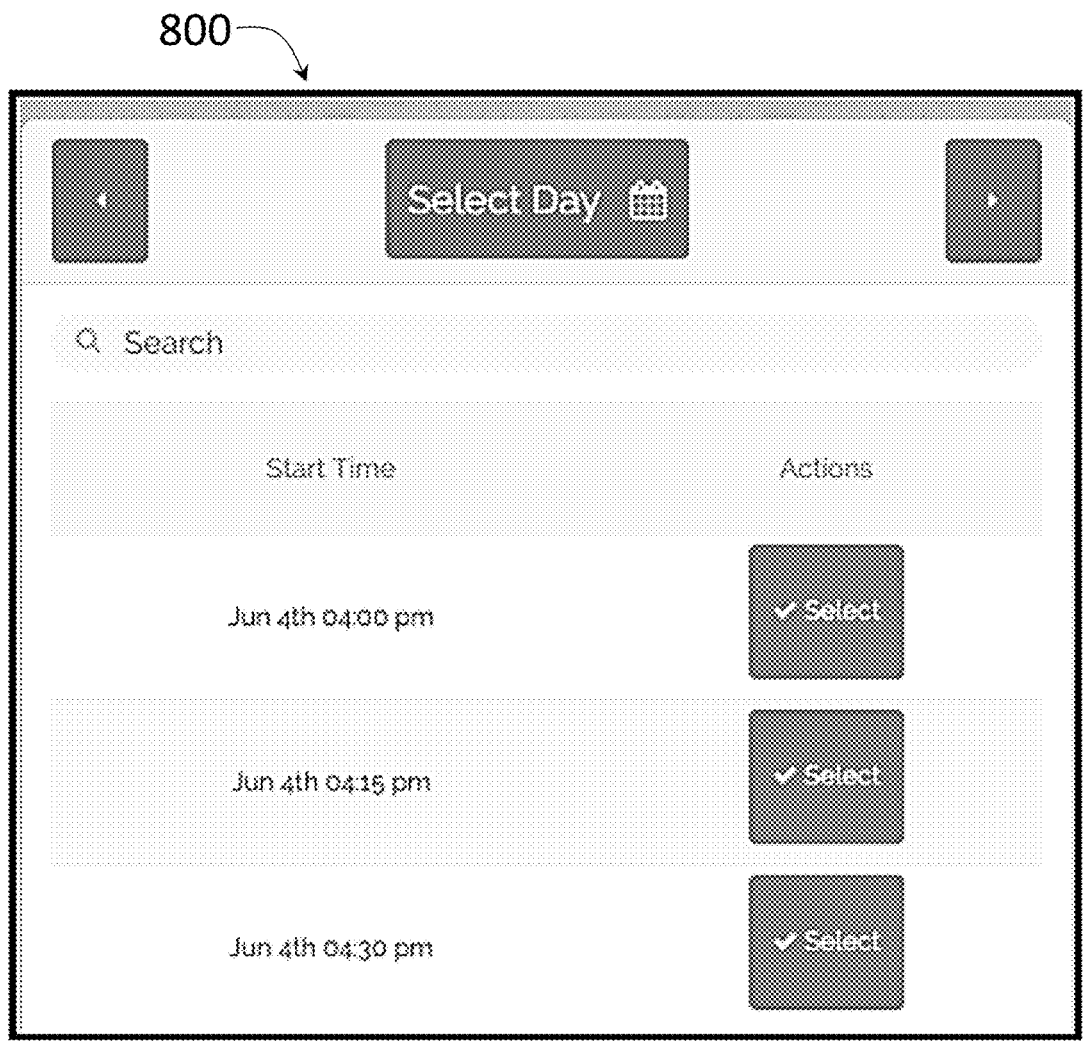
FIG. 8H is an exemplary scheduling interface.
Figure 8I:
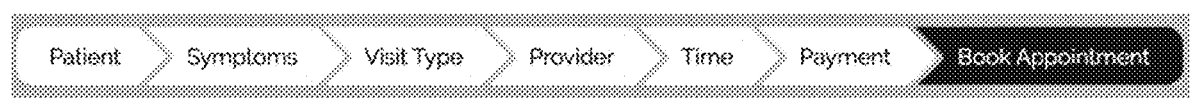
FIG. 8I is an exemplary scheduling interface.
Figure 10A:
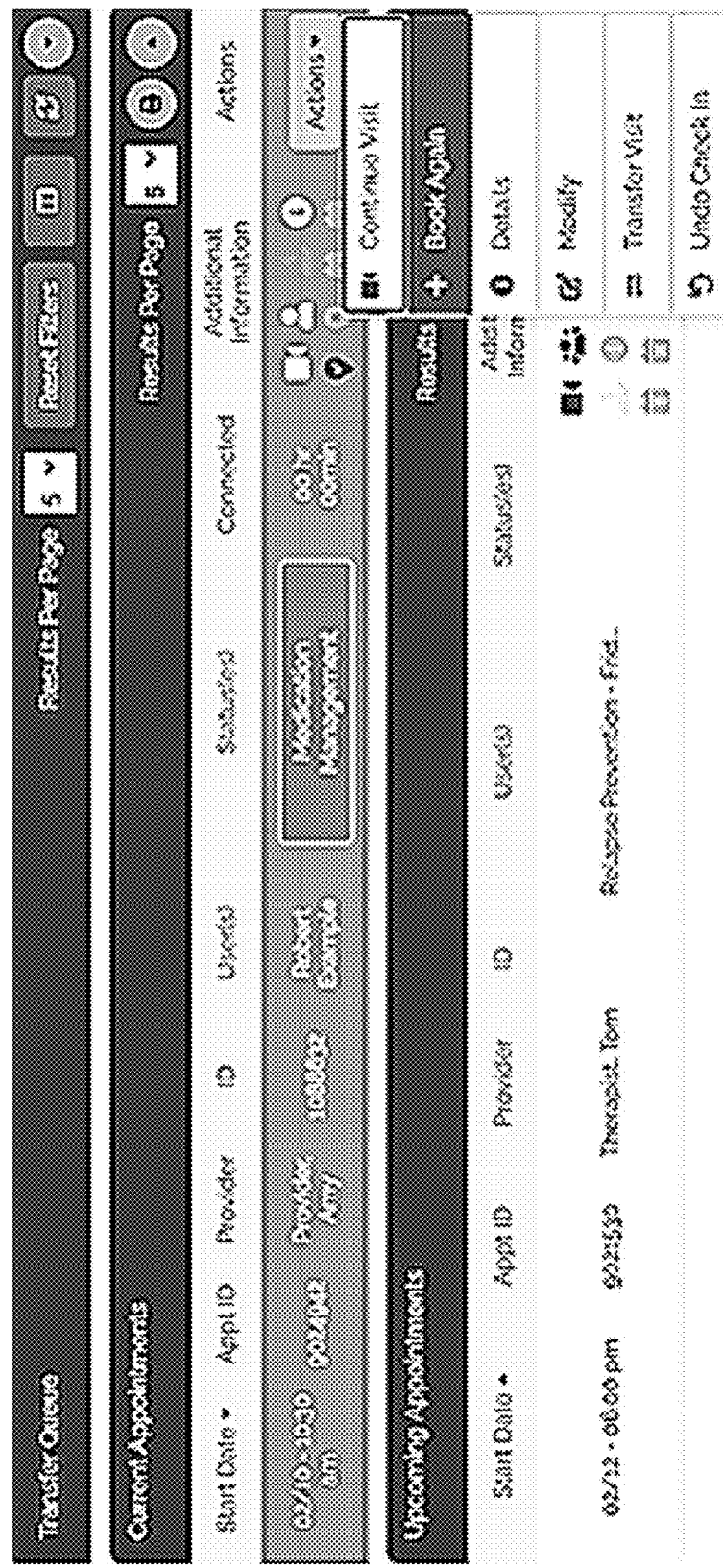
FIG. 10A is an exemplary scheduling interface.
Figure 10B:
FIG. 10B is an exemplary scheduling interface.
Figure 10B:
Figure 11B:
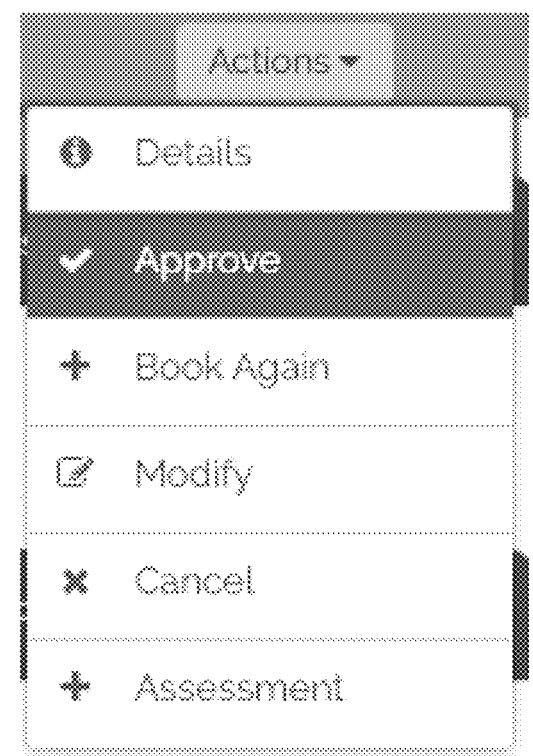
FIG. 11B is an exemplary scheduling interface.

According to another exemplary embodiment, shown in FIG. 6A-6C, an instant virtual exam room may be provided. Instant virtual exam room embodiments may be beneficial to organizations that use electronic health records as a master schedule. Instant virtual exam room embodiments may have advantages of reducing the burden of adding patients/users and virtual appointments to the system. Instant virtual exam room may also facilitate ensuring patients/users electronically sign legal agreements or review documentation before receiving services. Appointment records may also be created in the system, which may allow organizations to accurately track video metrics using a system report feature. An invitation for an instant virtual exam room visit may be sent to a mobile phone number or email address, which may be entered in a start window, similar to the initiation of an ad-hoc appointment. According to some further exemplary embodiments, a user or invitee may be selected from a stored list. Contact information associated with that user may be stored on a server and may be automatically used to communicate an instant virtual exam room invitation. When selected from a list, the invitation may be sent to one or more of an e-mail, a mobile number, or to a mobile device through a web or mobile application notification. Instant virtual exam room appointments may be set up for immediate connection or for a future time and may optionally be only available for video connection. The scheduler or provider may create a generic appointment on a dashboard and may join the visit from the dashboard.

A provider may invite a user/patient to a instant virtual exam room by logging in to the system. This may be done by navigating to and logging in to a webpage or opening a mobile application to access a dashboard 600. The provider may select to start an instant virtual exam room visit using a button 602 on a common actions menu of the dashboard, as shown in FIG. 6A. An instant virtual exam room window 604 may open, which may be shown in FIG. 6B. The instant virtual exam room appointment window may optionally include a provider field. This field may match a dashboard's displayed provider if the system is only displaying and/or the scheduler is only viewing one provider's appointments. The window may also show a start date and start time. The fields may auto-populate to a time within five minutes of scheduling. A duration may also be provided and may optionally default to 15 minutes. The duration selection may be set for scheduling purposes and may optionally not affect the actual duration of an appointment. The provider/scheduler may enter a user/patient name, email, or phone number in a search bar, which may show possible users/patients for selection to book an appointment. The patient/user and/or the provider may receive a secure link 606 to access the video visit. It may be possible for new users to set up an account upon receipt of an invitation from a provider. It may also be possible to disable self-signup and to instead allow an invited user/patient without an account to enter the appointment as an anonymous user. Anonymous user set-up may also bypass any consent documents. Once a provider sends an invitation, the invitation window may be closed and the system may be directed to the dashboard, where the appointment may be shown under an upcoming appointments section. When a user or patient joins a video conference, an indicator may be shown to the provider. For example, the upcoming appointment may turn green to signify that the invitee/user/patient has joined. The provider may begin the conference by selecting a start visit button. Upon completion, a hang up button may be used to exit the conference and return to a dashboard view.

According to an exemplary embodiment, a patient, user, or invitee and/or a provider may receive a secure video link upon creation of an appointment by a provider, scheduler, or the user/patient. Furthermore, a patient or user may receive reminders regarding an appointment, when applicable. A patient/user may be required to verify identify with a date of birth or may be required to create an account. The identity verification or account creation may optionally be required to join a visit or to create/schedule an appointment. According to some embodiments, user account creation may be disabled by request. Furthermore, a patient/user may be able to view and sign electronic consents or other forms when an appointment is scheduled or prior to joining a visit. Instant virtual exam room scheduling may also allow for tracking of video session metrics by an organization.

According to still further exemplary embodiments, a single-page booking embodiment of a video appointment scheduling system may be provided. A single-page booking embodiment may be beneficial for organizations that use electronic health records as a master schedule and for providers that prefer using a dashboard in "calendar view." In single-page booking, an invitation may be sent through a web or mobile application and may be sent by selecting a user/patient from a database of stored users. Single-page booking may allow for setting up appointments for an immediate or imminent timeframe or may allow for scheduling appointments at a future time. Single-page booking may also allow for scheduling video connections, in-person appointments, or kiosk video appointments. According to an exemplary embodiment, a kiosk video appointment may be for an in-office video appointment or for a video connection through a kiosk supported by the provider. This may allow for a user/patient to be in-office and conference with a provider that is out of office or in a different room. A kiosk visit may be helpful in minimizing or eliminating extended periods of in-person contact, which may minimize or prevent the spread of infectious diseases. A provider and user may optionally conduct all or some of an appointment using a kiosk. A portion of the appointment may also be in-person. The ability to perform parts of an appointment by video conference and only interact in-person for necessary portions of the appointment is beneficial for social distancing practices during times of need, such as pandemics. For implementation, a scheduler and/or provider may create an appointment on a dashboard in a calendar view. The single-page booking may allow for selecting from a number of providers, locations, and/or appointment types. The provider may also join the visit from the dashboard. A user/patient may receive appointment reminders, connection tests, and/or a secure video link through single-page booking systems. The user/patient may also verify identity with date of birth and may optionally sign electronic consents and/or complete intake forms, when applicable. An organization may track detailed video metrics.

Single-page appointment scheduling may include a shortcut for staff or providers to book an appointment with a single click in a dashboard calendar view, which may allow for bypassing the appointment type selection triage. Single-page scheduling may not be available for all organizations and may be beneficial for practices with limited types and minimal provider filtering in the scheduling process. Single-page scheduling may bypass all filtering options in the booking process and may instead allow selection of any provider for any appointment type or location. As shown in FIG. 7A-7F, an exemplary embodiment of a single-page scheduling system may be provided. To use single-page scheduling, a dashboard 700 may need to be in a Calendar View, which may be toggled with a List View/Calendar View button 702. The dashboard may also display a panel of calendar options 704 listing providers, visit types, and locations within an organization. To schedule an appointment, at least a provider must be selected. According to other embodiments, a provider and a visit type must be selected or identified. For in-person or office video/kiosk appointments, a location must also be selected. A time slot length, month, week, and/or day may be toggled for an appointment being scheduled using a date and time interface 706. Once the appointment details have been established, an open/available space on the calendar may be selected to create a new appointment slot. The slot can be dragged to modify or may be canceled by pressing an X or close button and to book the appointment, a check mark may be selected. When booking the appointment in a Book an Appointment window 708, a new patient may be added by selecting a plus sign instead of entering a name in the search bar or the search bar may be used to locate and select a user or patient existing in the system. The appointment type, location (if applicable), provider, and time slot may be pre-populated based on options chosen prior to clicking the desired slot; however, these fields may be changed through the Book an Appointment window. If all items are as desired, the scheduler/provider may select "Next," which may present a confirmation screen and the ability to "Book" and schedule the appointment.

Now referring to exemplary FIG. 8A-8I, there may also be a full appointment scheduling system and interface 800. A full appointment scheduling process may be beneficial for organizations that use the present system as a master schedule, organizations that have multi-specialty practices, organizations that have multi-location practices, and/or organizations that allow patient self-scheduling. According to an exemplary embodiment, invitations may be created and sent to a user/patient through the system and may utilize stored or entered contact information and/or notification through a web and/or software application. Full appointment scheduling systems may provide for booking of appointments for immediate conferencing or meeting at a future time. Furthermore, full appointment scheduling systems may set up appointments for video connections, in-person appointments, and/or office video/kiosk appointments. The scheduler and/or provider may utilize an appointment selection triage to ensure a correct provider, location, and appointment type are selected. The scheduler and/or provider may further join the visit from the dashboard. The patient may be able to receive appointment reminders, connection tests, and/or a secure video link. The patient may further optionally be able to verify identity using a date of birth and may sign electronic consents and/or complete intake forms when applicable. The providing organization may be able to track detailed metrics of appointments and video conferencing.

According to some exemplary embodiments, a payment may be sought by a scheduler/provider during the booking process. Scheduling a new appointment may be initiated by a scheduler or provider by selecting a button on a dashboard or by selecting a "plus" sign next to an appointments tab of the menu tab. The first step to schedule an appointment may be to select a patient, which may be done by locating an existing patient in a records database or by selecting to add a new patient to add a new patient to the patient list. Once a patient has been located or added, they may be selected for the appointment. The scheduler may then select whether the appointment is for an adult patient by selecting "Self" or "Dependent(s)" for appointments for a minor or individual under someone else's care. If Dependent(s) is selected, additional information may be required, such as selection of a stored list of individuals associated with the account including a parent or guardian and any associated dependents.

Next, an appointment selection triage page of the system may be provided. The triage page may be customizable based on organization protocols and may be intended to help guide schedulers and providers to ensure appropriate appointment types are selected for a user/patient. The triage page may present a number of questions to guide the scheduling process. For example, the triage questions may focus on the patient type (new or established, adult or pediatric, insurance or self pay, etc.) or the provider type they are seeking (specialist, medical doctor, therapist, etc.). The triage system ay also ask to verify a patient's complaints are appropriate for the appointment type. According to organizational determination, various appointment types may be provided. For example, video appointments may be provided where patients and providers connect face-to-face from different remote locations using their own devices, office video appointments may be provided where patients present to an office location and use a kiosk device to connect face-to-face with a provider in a remote location or another area of the office location, in-person appointments where a patient presents to a physical location and meets with a provider in that location, and messaging appointments where a patient and provider communicate asynchronously in a messaging chain. If scheduling an office video or in-person visit, a scheduler may be prompted to select a location as an additional step. Furthermore, a list of providers available for an appointment may be filtered based on the appointment type selected, provider credentials or specialty, age of the patient, and/or the location(s) where the provider is available. Likewise, a list of appointment types available under a provider may be filtered based on the provider. A selection of open slots, if any, may be shown next to each respective provider. For example, the next three open slots may be shown and a "more" option for viewing additional slots may be provided. The "more" selection may reveal a full calendar screen, which may allow for selecting an appointment date and time by clicking an open space. When an open space is clicked, a green "New Appointment" icon may appear, which may be clicked and dragged to a desired slot on the screen. When in a desired place, a "Set Selected Date" option may be entered. The calendar may include a mobile-friendly version. The full calendar may optionally have arrows for navigation and/or a "Select Day" entry for jumping to a desired date. A time may be selected using a "Select" button. A payment method may also be selected for booking. Lastly, the appointment details may be confirmed by scrolling through the page-by-page information. Once checked, the appointment may be scheduling by selecting "Book" or "Charge" if a payment step is required. Once booked, the appointment may be added to the provider's upcoming appointments and a first patient or user notification may be sent by at least one of email and text message.

Referring to FIG. 9A-9B, and according to still further exemplary embodiments, a group appointment scheduling process, system and interface 900 may be provided. Group appointments may allow for inviting multiple users to a single appointment, whether in-person or on a secure video connection. Group appointments may be scheduled on a one-time or recurring basis. To begin setting up a group appointment, a group must be stablished. Using an add group selection, the system may collect information including some or all of a group name and description. The name may be visible to the users and/or patients in the group, but the description may optionally only be visible to providers, staff, and the provider organization. The group may then be completed by selecting users from the stored database or optionally by adding new user information. Once a group has been saved, a number of actions may be provided, including scheduling a single appointment for the group, setting a regularly recurring appointment schedule for the group, assigning a form or assessment to all group members, viewing the details of the group that has been created, inviting new patients, staff, or providers to the appointment or removing existing users using an edit function, or clearing the group form the available group appointments that may be booked using a delete function. According to a single group appointment process, the booking process may be triggered from an "Actions" menu on a groups page or a button on the dashboard. The single group appointment booking process may be similar to that for an individual appointment. Each individual in a group may receive at least one of text or email reminders with instructions and a unique secure link to connect. For recurring schedule appointments, a regularly recurring schedule for the group may be facilitated. If a Group Scheduling Enabled selection is turned on, appointments may be booked automatically according to a set frequency. When saved, all members of a group may be notified that they have been scheduled for a recurring group appointment. Furthermore, each individual may receive reminders with instructions and a unique secure link. According to some embodiments, a reminder and link may be provided 24 hours prior to each session and again 30 minutes before each session. For a provider to join a group video appointment, the appointment may be selected from their calendar or, if initiated by another provider or staff, the appointment may be accessed by following a link in a provided notification or reminder regarding scheduling of the appointment.

Now referring to exemplary FIG. 10A-10D, a book again process, system, and interface 1000 may be provided. According to the book again feature, a shortcut may be provided to schedule another appointment for the same patient with the same provider. This option may typically be used to schedule follow-up appointments. When a provider selects to book again, a prompt may ask whether the provider is scheduling the appointment or whether the provider is allowing the patient to schedule 1010. If the provider selects to schedule themselves, the provider's calendar may be shown 1020. An available time may then be selected to schedule the appointment and, if applicable, the appointment type may be added. If the organizational preferences allow the system to support Recalls, the provider may choose between scheduling the appointment now or sending the patient a reminder to book on a future date 1030. In Recalls embodiments, after selecting book again and selecting to let the patient schedule, a future date may be selected for an appointment scheduling reminder to be sent to a patient. The Recall may then be scheduled and the date confirmed.

Now referring to exemplary FIG. 11A-11F, unapproved appointments and pending requests processes, systems, and interfaces 1100 may be provided. Unapproved appointments and pending requests sections may be available through a dashboard, if permitted by an organization. Unapproved appointments may be available where an organization allows patient self-scheduling, but requires a provider or staff member to approve self-scheduled appointments and where an organization allows patient self-scheduling but does not require provider or staff approval, but instead all appointments scheduled by patients are routed directly as upcoming appointments. If a patient requests to cancel or reschedule an appointment, it may be shown in a pending requests section. When a patient self-schedules an appointment, a notification may be provided that the appointment is pending approval. An associated provider may also receive a notification prompting them to select at least one of approve, modify, or deny the appointment. In addition to approve and modify selections, a details selection may display patient and appointment information, a book again selection may provide a shortcut to schedule a follow-up appointment of the same type for the patient, a cancel selection may cancel the appointment and remove it from the dashboard, and an assessment selection may provide a shortcut to send a form to the patient. Selecting approve may prompt the appointment to move from an unapproved appointments list to an upcoming appointments list. The upcoming appointments list on the dashboard may show appointments for a predetermined upcoming range and a full upcoming appointments list may be provided on a more detailed appointments page. Selecting approve may also send a notification to the patient to confirm the appointment has been scheduled and presenting all instructions necessary to connect. Selecting modify may present a modify appointment window, which may show patient information and may allow for editing of appointment type, provider, location (if applicable), date and time, check in, and symptoms. Upon saving modifications, the appointment may automatically be approved. According to a pending requests section, if an organization allows patients to reschedule or cancel appointments, patients may do so from a secure link in their notifications or by logging in to their account. All requests to cancel or reschedule appointments may optionally appear under a pending requests section on a dashboard. A provider may view the appointment requests, including pending cancellations or pending reschedule requests. According to some exemplary embodiments, an organization may request a patient reason, which may be displayed with the pending request. A provider may then approve or deny the request from the pending requests section.

According to an exemplary embodiment, a virtual waiting room may be provided. The virtual waiting room may present a blank screen or may optionally present a screen showing instructions to remain connected awaiting the other participant(s). A virtual waiting room may be entered when accessing a scheduled appointment and awaiting other participants or when a user schedules to be seen immediately. According to some embodiment, a virtual waiting room may be presented until a provider selects to start an appointment and/or when a provider or user leaves an appointment or temporarily puts an appointment on hold. Controls for in-meeting actions and preferences may optionally be available while waiting. Furthermore, consents, documents for electronic signature or other informational documents may be accessed and/or completed by a provider, patient, or user in the virtual waiting room. According to some embodiments, a small window or picture-in-picture within the virtual waiting room may show the view through the respective user's camera displayed to the other meeting participant(s).

Figure 12C:
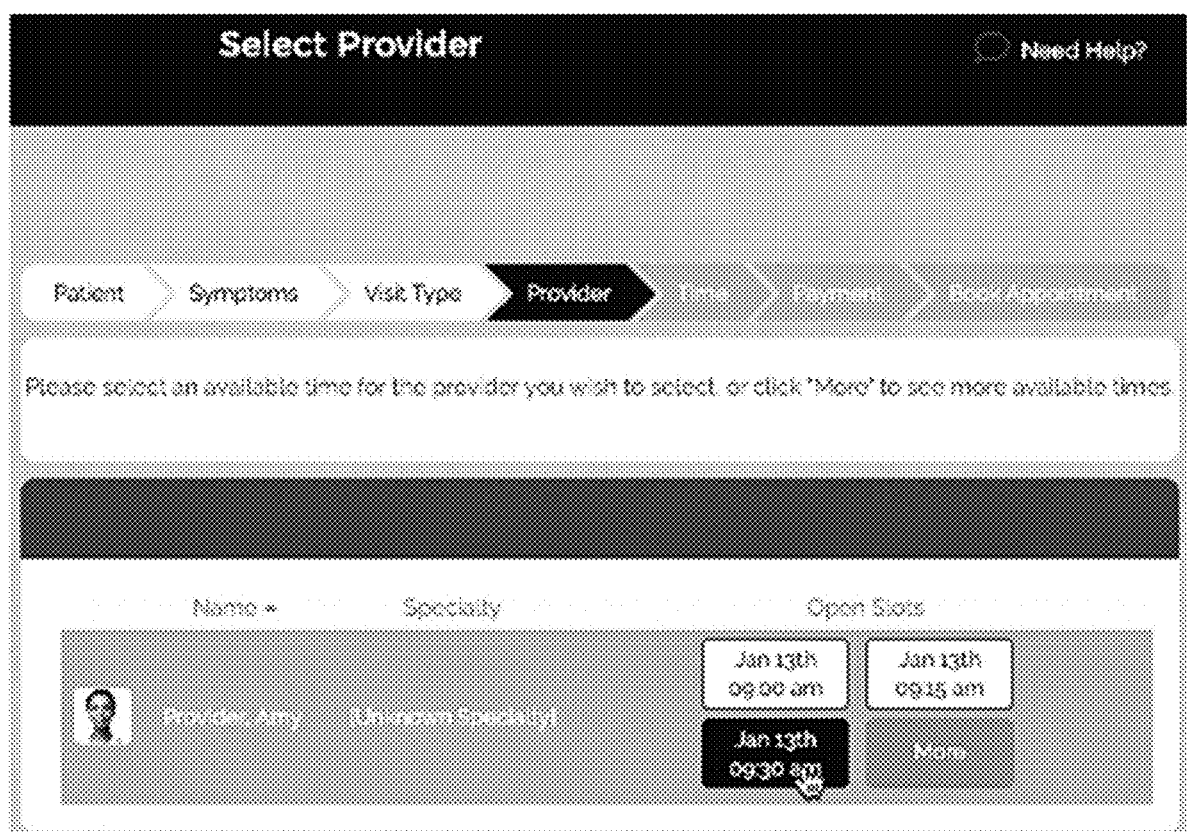
FIG. 12C is an exemplary scheduling interface.
Figure 12D:
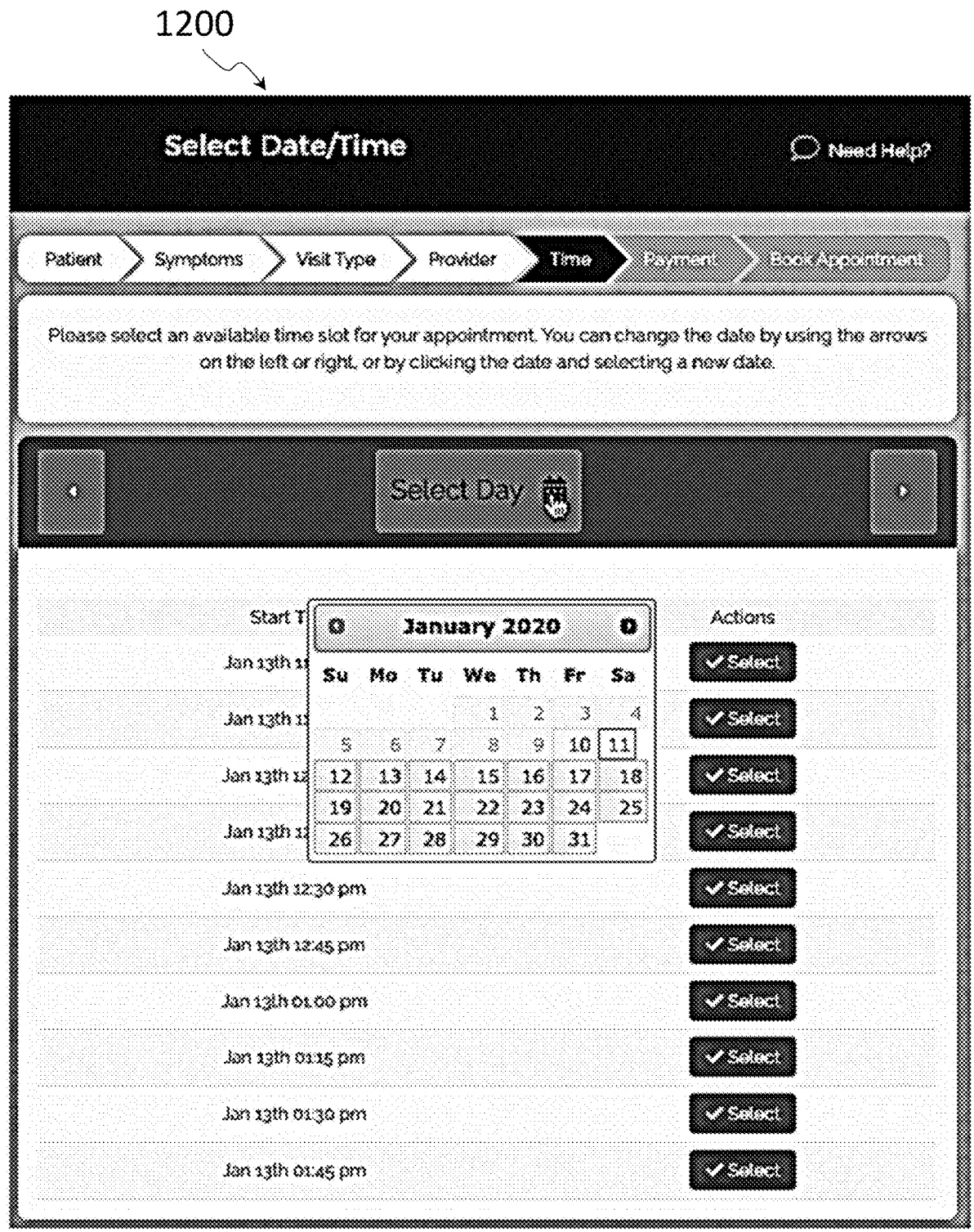
FIG. 12D is an exemplary scheduling interface.
Figure 12E:
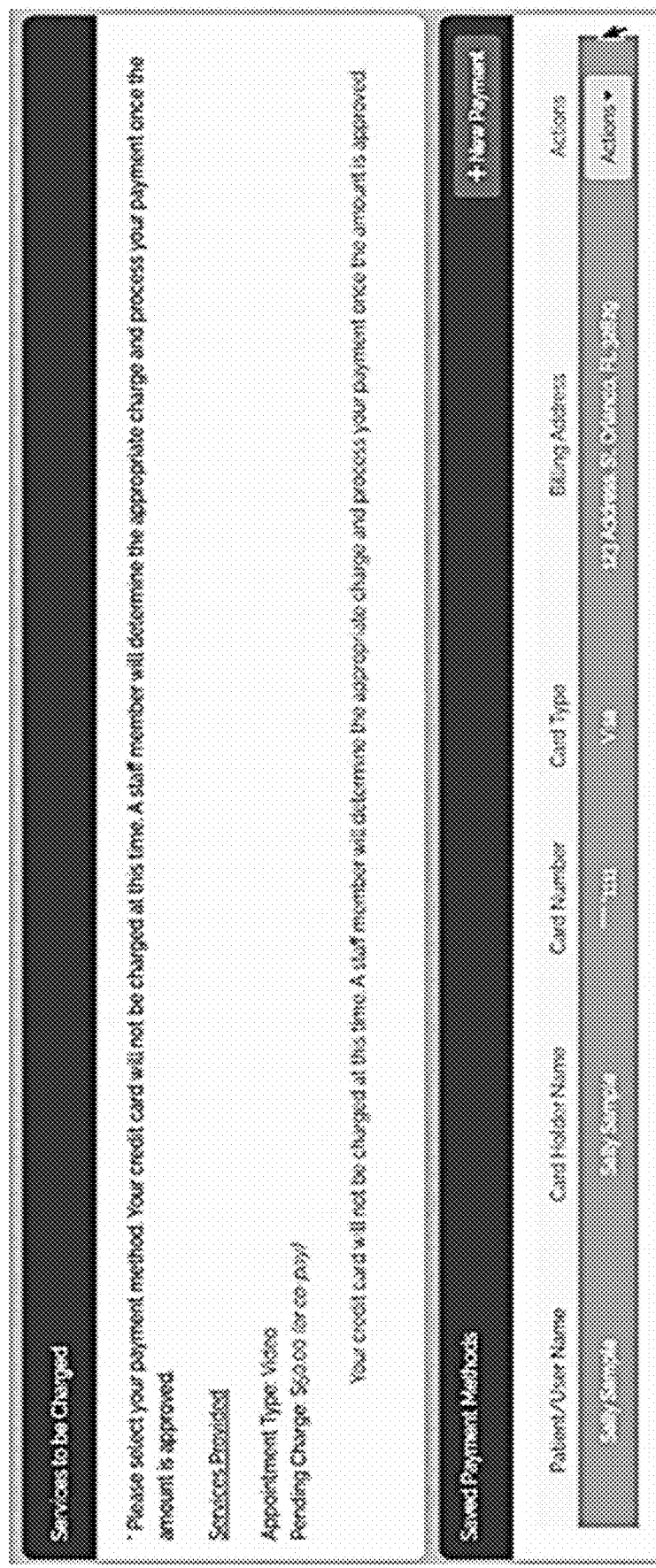
FIG. 12E is an exemplary scheduling interface.

Now referring to exemplary FIG. 12, a patient/end user appointment scheduling process and interface 1200 may be described. An organization may allow patients to do some or all of self-schedule, re-schedule, confirm, and/or cancel an appointment. A user may create an account and/or login to a system account through a webpage portal or software application. The user may then be presented with a dashboard, which may provide at least one of tasks, action items, preferences, and personal information. Through a user dashboard, a user may access forms and downloadable information. Furthermore, a user may select to schedule an appointment. When booking an appointment, a select patient option may be presented. Patients may be able to book appointments for themselves or for any applicable dependents. If selecting a dependent, an additional screen may be presented to specify the dependent. Patient information may be entered and stored with an account prior to booking an appointment. Once a patient has been selected, a reason for a visit may be entered. According to organizational preferences, a reason may be selected from a pre-set list, entered in free-form text, or skippable. A visit type may also be entered. When entering a visit type, the system may collect some or all of the following information: where the patient is located, whether it is a new patient, whether symptoms are listed on a preset list, how the appointment will be paid for, and if a specialist is needed, such as therapy, medication management, dermatology, podiatry, and other specialists as would be understood in the art. The system may also seek information on whether the patient/user would like to book a future appointment or be seen immediately. For immediate appointments, it may be possible to immediately reroute a patient to a virtual waiting room. A patient/user may select a provider from a list, which may be filtered based on a number of factors, such as type of care and availability. Once filtered, any provider available may be selected for an appointment. Open time slots shown may be selected or an option may be selected to see more options, which may present a scrollable list view and/or a calendar view. Organizational preferences may also request payment information to pay a co-pay or full self-payment. Once a patient enters payment information, it may be charged immediately and stored or deleted, or may be stored for payment at a later date and/or future appointments, depending on organizational preferences. The system may present appointment information to review and confirm. Once approved and "booked" by the patient, organizational preferences may require approval from a provider or may allow the appointment to be booked if no approval is required. A patient or user may receive an appointment confirmation showing one or more of the following: appointment date and time, a provider's name, a link to confirm the appointment, a link to cancel or reschedule (if applicable), a location and directions (if applicable), and for video appointments, a link to test a browser, camera, microphone, speaker, and internet connection, a secure link to connect to the appointment, and a unique code to connect to the appointment and/or a unique code to connect to the appointment on a mobile device (when applicable).

Once booked, an end user or patient may be able to reschedule and/or cancel an appointment according to organizational preferences. To reschedule, a user may select a reschedule option from a user dashboard or appointments page. A unique link to reschedule and/or cancel an appointment may also be sent to a user in an appointment notification, such as a confirmation or reminder e-mail or text message. A user may be required to verify identity by entering a date of birth before being authorized to reschedule or cancel an appointment. When rescheduling, additional timeslots may be presented to the user. Alternative time slots may be selected on the same day or additional days. For canceling, a cancel option may be provided. According to organizational preferences, a reason may be required for rescheduling and/or canceling. Once an appointment is rescheduled or canceled from a patient, it may be automatically approved or in some embodiments it may be pending approval from a provider. The provider may be alerted to the requested change and may approve, deny, or modify the reschedule or cancelation.

The above descriptions may list certain features associated with different scheduling system options; however, it may be understood that each of the above-described features may be used in any combination for various embodiments of the system.

Figure 13:
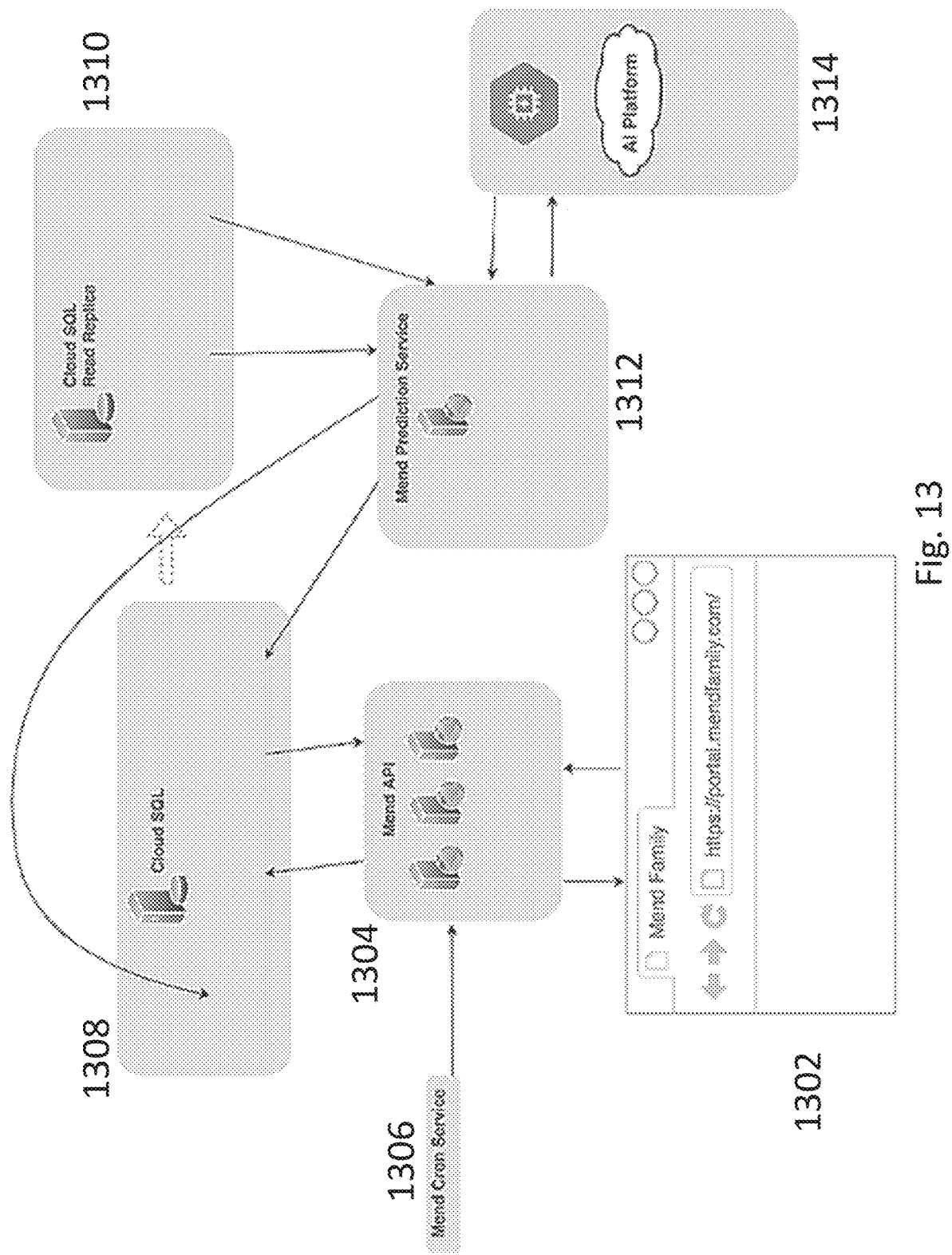
FIG. 13 is an exemplary diagram showing system architecture for a prediction system.
Figure 14:
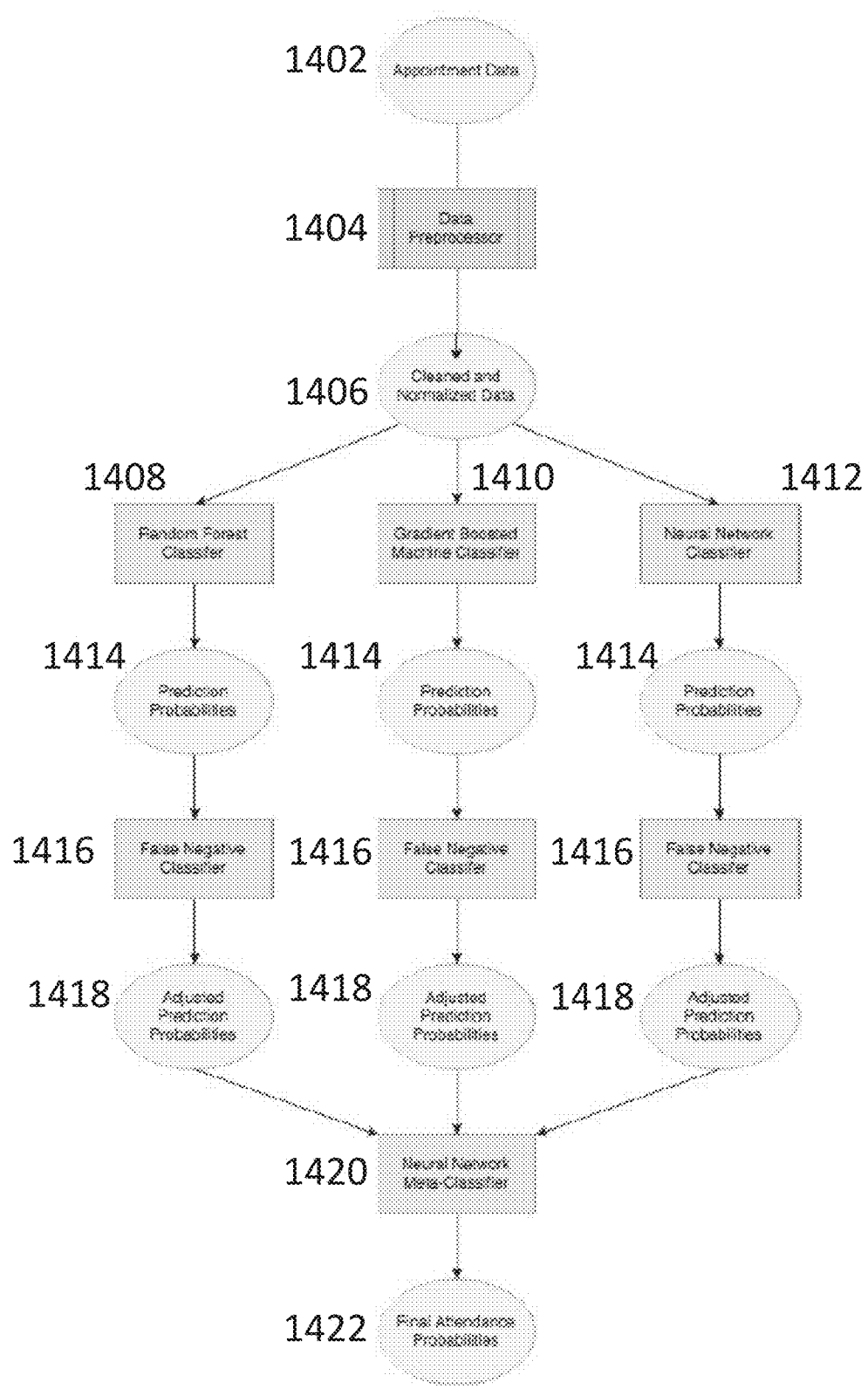
FIG. 14 is an exemplary diagram showing a machine learning process.

Now referring to exemplary FIGS. 13 and 14, a predictive scheduling application for identifying appointment cancellations, no-shows, and high-risk appointments may be provided. A high-risk appointment may be categorized based on an assigned probability of cancellation or no-show. There may be a customizable threshold probability for consideration as a high-risk appointment. For example, one embodiment may associate a high-risk label to any appointment in which the high-risk probability is above a certain number, e.g. 40 on a scale from 0-100, while others may utilize a different threshold number. Additionally, in cases in which an organization's appointment outcome history does not cleanly map to a 0-100 risk scale (for example, in the case that averaged appointment data reports a significant risk for many appointments but that risk is not reflected in reality), the risk score may be normalized to a different scale, e.g. between 20 and 100, between 0 and 80, etc. This may allow for the predictive scheduling application to communicate scores that are clearly understandable to a user. The predictive scheduling application may use machine learning and or artificial intelligence (AI) to obtain and analyze factors, which may be applied to a predictive model for determining appointment cancellations and no-shows. The exchange of any patient information and appointment data may be made in a safe, secure and HIPAA compliant manner. Factors used by the predictive scheduling application may include, for example, demographic data, appointment data, patient scheduling data, and/or patient form data. Additional data factors for training models and generating predictions may include, but not be limited to, time between appointment scheduling and actual appointment date (in other words, how far in advance an appointment was made), which may be measured in any desired increments including days or months; date and time of an appointment, appointment type (video, office, or kiosk); patient and/or guardian, if applicable, confirmation status for the appointment; prior login of patient and/or guardian, if applicable; completion of appointment connection test; past history of high-risk outcomes of patient, such as prior cancellations or no-shows; basic patient demographics, such as age, gender, presence of valid contact information; past history of high-risk outcomes of provider, such as prior cancellations or no-shows; basic provider demographic, such as age and gender; provider specialty; and appointment density of both patient and provider, including how many appointments in a given time period. This non-exclusive list of factors may be applied to a scoring algorithm or otherwise correlated to a risk probability scale, as would be understood by a person having ordinary skill in the art.

Referring to exemplary FIG. 13, a diagram showing a system architecture and an overall flow of actions and data for the prediction system may be provided. A user interface or website 1302 may be provided, which may show a likelihood of appointment attendance and which may allow for on demand attendance prediction requests. According to some exemplary embodiments, this may be a unique interface from a patient interface for scheduling and/or requesting an appointment and may instead by a provider interface which may optionally be accessible only by a provider or scheduler. The interface 1302 may receive prediction data for each appointment from an Application Programming Interface (API) 1304 and may communicate prediction requests to the API 1304. A software scheduler 1306 may also communicate appointment data to the API 1304 to request predictions for approaching appointments on a daily basis. The API 1304 may manage prediction requests for new appointments, updated appointments, and approaching appointments. The API 1304 may communicate with a database 1308. Specifically, the API 1304 may communicate appointment requests to the database 1308 and may receive appointment prediction data from the database 1308. The database 1308 may be a cloud-based database. The database 1308 may be used to create a database read replica 1310, which may include appointment prediction request data and appointment and user data. The requests and appointment and user data may be read or processed by a prediction service 1312. The system may employ a microservices architecture and the prediction service may be a microservice. The prediction service 1312 may read enqueued requests for predictions from the database read replica 1310 and may send requests containing formatted instance data to an AI platform 1314. The prediction service 1312 may also save prediction records from the AI platform 1314 to the database 1308 and may mark requests as complete in the database 1308. The AI platform may include one or more served models. Models may be trained and uploaded manually. According to some further exemplary embodiments, a pipeline may automatically train new models and serve them. The AI platform 1314 may communicate predictions to the prediction service microservice 1312, which may save predictions to database 1308 and mark requests as complete in database 1308, as detailed above. The predictions may then be communicated to and/or accessed by the API and may then be displayed through interface 1302.

According to an exemplary embodiment, the predictive scheduling application or prediction platform and system may utilize several stages, each employing state-of-the-art processes and leveraging the latest capabilities of machine learning. To ensure optimal accuracy and bolster the strength of predictions made by the prediction platform, the platform may combine multiple types of inference engines or machine learning modules.

The platform may include a modular structure, which may employ multiple stages that can each be independently tweaked by changing values in a respective section of a configuration file or files. To initiate the prediction platform, a provider or user may trigger a request to generate a prediction regarding the probability of a high-risk outcome for an appointment through either a creation or update action and/or an internal server may trigger a daily calculation of upcoming appointments. Other possible triggers for initiating the prediction platform may be understood by a person having ordinary skill in the art. According to still further exemplary embodiments, a prediction platform may run periodically and/or continuously to automatically audit scheduled appointments and to provide updated appointment status and/or classification based on the prediction outcomes. The system may have an appointment data store and may also create and utilize read replica of the appointment data store. An application programming interface (API) may make a query to a read replica of the appointment datastore. This may ensure client data is protected and that patient care cannot be interrupted through database operations on a main datastore. In addition to preventing corruption of a main data store, preventing interruption of patient care, and ensuring data protection and privacy, creating and utilizing a read replica of the appointment data store may improve computing performance for the prediction process and for actions involving the main data store by reducing respective traffic and requests on each resource. The data stores may be cloud based or may be stored on one or more local servers. The read replica may reflect changes to the primary or main appointment data store in real-time or near real-time, as would be understood by a person having ordinary skill in the art. A scheduling system may retrieve relevant appointment data and send a request to the prediction system.

Referring to exemplary FIG. 14, a diagram detailing a machine learning component of the prediction system may be provided. Upon receiving a prediction request, the appointment data 1402 may be formatted into a standard format and then may be passed to a prediction pipeline. In the prediction pipeline, the first stage may be a data pre-processor 1404. The data pre-processor may be a sub-pipeline, which may strip superfluous descriptors, drop unnecessary columns, encode certain time-cycle features, impute missing values for each feature, and then independently encode each feature, if necessary. The data pre-processor may yield cleaned and normalized data 1406.

According to an exemplary embodiment, the data pre-processor may strip superfluous strings. At this stage, data type labels from internal data may be stripped out. Since the appointment scheduling and remote conferencing platform may interact with data using a variety of technologies, strings may be appended to labels in a database so that engineers and users may easily determine how to work with the data. While the added strings may provide efficiencies when working with the data, these added strings are not necessary for the prediction system. By removing these added strings, the system may be optimized. This may improve computing performance.

Furthermore, the data pre-processor may drop any unnecessary columns or features. These features may be defined by a user prior to runtime using a configuration file. Dropping unnecessary features may reduce the magnitude of features that are to be processed, improving performance, and can also be leveraged to protect privacy of users by removing sensitive features, if such sensitive features were ever present. The pre-processor stage may be leveraged in the prediction system to ensure that predictions do not suffer from a phenomenon known as overfitting. Overfitting may refer to a trend in a predictive model in which the model's learned representation of the data is too specific to training data, which may lead to poor predictions. This is a critical flaw to avoid in machine learning platforms. In order for models to generalize across features, all features must have some sort of constraint on their respective set of possible values, such that same-feature commonality exists between instances. In other words, the model must not use any features for which the values cannot possibly be the same between two appointments.

Next in the pre-processor stage, the system may utilize a cyclical encoder to process certain data. Models may try to learn the representation of features, whether they may be continuous on a range from one number to another or discrete between different categories. For example, in many databases and computer systems, dates may be represented in human-readable formats, such as January: 1, February: 2, etc. However, machine learning models may interpret these "time-cycle" values as having a larger magnitude or importance, when they are, in fact, of the same importance. In order to prevent inaccurate representations from being learned by the base models, this equality may be instilled in the machine learning models. This may be accomplished by projecting the date values onto a unit circle, which may allow their magnitudes to remain the same while giving each possible value a different position in a project space. This may force the models to learn that all values in such special features are equally valid and have a relation to one another.

Additionally, classifiers may not be capable of dealing with missing values, which may require an imputation stage for accurate modeling. Therefore, all missing values may be corrected at the pre-processor stage. For example, some data types may be collected by a system provider for appointment requests, which may not be collected by a client organization. This may lead to instances in which an appointment request may have missing data. While other stages may remove such features, it is possible that some instances may remain. Therefore, all empty cells must be accounted for and filled. The system may utilize different strategies to fill empty cells, depending on the type of feature in which it occurs. According to an exemplary embodiment, the system may fill cells according to a predetermined number or string, which may be assigned to the empty cell.

Lastly, the pre-processor stage may perform label encoding, which may translate human-readable string values into a format that can be understood by the machine learning models, which may not understand human-readable string values. In this step, which may optionally be a last step of the pre-processing pipeline, each categorical feature may be label encoded, whereby each of the discrete values in that feature may be replaced with an integer value that may correspond to that feature. Therefore, any string that may be supplied by an organization for a certain feature may be mapped to an understandable format for the predictive models. The label encoding stage may also mitigate other harmful phenomenon in machine learning, such as data leakage. Data leakage is an event in which data that would not be available at prediction time is included in a model's learned representation after undergoing training. Since models leverage all data available during training in order to increase accuracy, the presence of data during training that will not be available when making actual predictions may result in reduced prediction accuracy or completely wrong predictions.

Once the pre-processor stage is complete, the resultant data may be given to a base classifier group. According to an exemplary embodiment, this may include a random forest ensemble, gradient boosted machine model, and neural network. Predictions for each model type in the group may then be analyzed by a group of false negative classifiers. If, and only if, a false negative is detected for an appointment, then the prediction for that particular appointment may be adjusted. Resultant probabilities may then subsequently be collated and sent to a final stage, which may be a meta-classification model. The system may generate a final risk score using predictions from the base models. A human-readable confidence string may be assigned depending on the magnitude of a risk score. The metrics may be paired together for each appointment instance that the prediction system was tasked with predicting and all instances may be collected into an easily communicable payload. The payload may then be returned by the prediction system to the API, which may then send changes to a front-end. Providers may be able to see the probability of a high-risk outcome, which may allow them to make more informed decisions about a patient's appointment.

According to an exemplary embodiment and as summarized above, after appointment data is pre-processed, it may be passed to the classification stage. The prediction may employ three separate model types in an ensemble: a random forest classifier 1408, a gradient boosted machine classifier 1410, and a neural network classifier 1412. The classification stage may be completely modular, which may allow for the possibility of replacing a model type or further strengthening the network through addition of a more accurate model type. In some embodiments, each model type used may be industry-trusted; however, the overall structure of the present system may differ by leveraging a model of each type to capture the advantages and mitigate the disadvantages of the respective model types through unique customizations. According some alternative embodiments the classification stage may employ less model types, as would be understood by a person having ordinary skill in the art.

All models may be encapsulated in a standard interface in order to optimize the throughput of the prediction system. Pre-processed appointment data, or cleaned and normalized data 1406, may be passed to each of the models and base predictions, or prediction probabilities 1414 may be generated from this data. The base predictions may then be analyzed by another set of classifiers that may be trained to detect false negatives, a false negative classifier 1416. According to an exemplary embodiment, false negatives may be predictions indicating that an appointment will not result in a high-risk outcome, but the appointment does, in fact, result in a no show or cancellation. Reducing false negatives, such as this, are important for successfully optimizing the system. Therefore, a negative classifier is associated with each model type. If a false negative occurrence is detected, the original base prediction may be adjusted to reflect the uncertainty, yielding adjusted prediction probabilities 1418. After a false negative detection stage, all appointment predictions, which may be adjusted prediction probabilities 1418, may be passed onto a meta-classification stage. At the meta-classification stage, each appointment may have its base predictions from each model type associated together and a meta-classifier 1420 may make a final prediction 1422 or yield final attendance probabilities 1422. According to some exemplary embodiments, the meta-classifier may be a neural network type classifier 1420.

The above described classifier arrangement may enable using more information for predicting an outcome while also keeping computational requirements to an optimally small and fast level. The described classifier arrangement enables more information through the diversity and variety of its constituent approaches. Each of the classifier types also gives metadata that, while not necessarily in-use at a particular moment in time, may give additional insight into respective predictions of the classifier. For example, one type of classifier may give information about feature importance, which may facilitate making informed decisions on whether to include a feature (creating a leaner model as there are fewer calculations to make) or increase the weight of said feature (potentially leading to more accurate predictions). Each classifier type has metadata that can be used to improve those two goals: a smaller/faster model, and a more accurate model. In embodiments using multiple types of classifiers, leveraging other types of metadata that could aid in further refinement of models may be made possible, which may improve performance.

According to some exemplary embodiments, the classification may be structured such that each model type is provided with different appointment data, which may or may not overlap, to optimize the effectiveness of respective models or the combination of models. Alternatively, each model type may be provided with identical appointment data, as would be understood by a person having ordinary skill in the art.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art (for example, features associated with certain configurations of the invention may instead be associated with any other configurations of the invention, as desired).

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A method for providing an efficient and secure interface for transferring protected electronic information, comprising:
   providing a transfer page, the transfer page comprising a web page supporting at least one of uploading of protected electronic information, submission of intake forms, or live video or audio conferencing;
   generating and providing, from a server to a user device or kiosk, a unique access link to access the transfer page, the unique access link comprising a uniform resource locator (URL) directed to the transfer page, wherein the unique access link is sent by one or more of email, SMS, or push notification;
   requesting entry of a personal identifier when the unique access link is accessed, the personal identifier comprising at least one of a record of the user or an identification of at least one personal characteristic of the user;
   receiving the personal identifier from the user device or kiosk;
   verifying the personal identifier by comparing the personal identifier with a previously stored set of personally identifiable information;
   when the personal identifier is verified, granting the user device or kiosk access to transfer protected electronic information, submit intake forms, or connect to live video or audio conferencing on the transfer page; and
   wherein the transfer page is a no-login page using identity verification for transferring electronic information, submitting intake forms, or connecting to live video or audio conferencing.

2. The method of claim 1, wherein the unique access link expires after a set time interval.

3. The method of claim 1, wherein the user device or kiosk is connected to a real-time audio, video, or audio/video conference.

4. The method of claim 1, wherein identity verification requires data captured in real-time by a user device or kiosk.

5. The method of claim 1, wherein the personal identifier is collected during account creation.

6. The method of claim 1, wherein the personal identifier is a date of birth.

7. The method of claim 5, wherein account creation privileges are restricted to providers.

8. A system for providing an efficient and secure interface for transferring protected electronic information, the system comprising a server device and a network connection, the server device being configured to execute steps comprising:

providing a transfer page, the transfer page comprising a web page supporting at least one of uploading of protected electronic information, submission of intake forms, or live video or audio conferencing;

generating and providing, from a server to a user device or kiosk, a unique access link to access the transfer page, the unique access link comprising a uniform resource locator (URL) directed to the transfer page, wherein the unique access link is sent by one or more of email, SMS, or push notification;

requesting entry of a personal identifier when the unique access link is accessed, the personal identifier comprising at least one of a record of the user or an identification of at least one personal characteristic of the user;

receiving the personal identifier from the user device or kiosk;

verifying the personal identifier by comparing the personal identifier with a previously stored set of personally identifiable information;

when the personal identifier is verified, granting the user device or kiosk access to transfer protected electronic information, submit intake forms, or connect to live video or audio conferencing on the transfer page; and wherein the transfer page is a no-login page using identity verification for transferring electronic information, submitting intake forms, or connecting to live video or audio conferencing.

9. The system of claim 8, wherein the unique access link expires after a set time interval.

10. The method of claim 8, wherein the user device or kiosk is connected to a real-time audio, video, or audio/video conference.

11. The system of claim 8, wherein identity verification requires data captured in real-time by a user device or kiosk.

12. The system of claim 8, wherein the personal identifier is collected during account creation.

13. The system of claim 8, wherein the personal identifier is a date of birth.

14. The system of claim 12, wherein account creation privileges are restricted to providers.

15. A non-transitory computer readable medium having stored thereon software instructions that, when executed by a processor, cause the processor to:

receive, from a server, a unique access link directed to a transfer page, wherein the transfer page supports at least one of transfer of protected electronic information, submission of intake forms, or live video or audio conferencing;

request access to the transfer page using a personal identifier comprising at least one of a record of a user or an identification of at least one personal characteristic of the user, wherein the personal identifier is among a previously stored set of personally identifiable information associated with an account;

upon verification of the personal identifier, access the transfer page to transfer protected electronic information, submit intake forms, or connect to live video or audio conferencing on the transfer page;

wherein the transfer page is a no-login page using identity verification for uploading electronic information, submitting intake forms, or connecting to live video or audio conferencing.

16. The non-transitory computer readable medium of claim 15, wherein the unique access link expires after a predetermined time interval or after being followed a predetermined number of times.

17. The non-transitory computer readable medium of claim 15, further comprising capturing real time data using a camera, audio recording device, or graphical user interface for identity verification and sending the real time data to a server for verification.

18. The non-transitory computer readable medium of claim 15, wherein the personal identifier is collected during account creation.

19. The non-transitory computer readable medium of claim 15, wherein the personal identifier is a date of birth.

20. The non-transitory computer readable medium of claim 18, wherein account creation privileges are restricted to providers.

* * * * *